(12) United States Patent
Li et al.

(10) Patent No.: US 12,138,102 B2
(45) Date of Patent: Nov. 12, 2024

(54) SYSTEMS AND METHODS FOR DETERMINING EXAMINATION PARAMETERS

(71) Applicant: SHANGHAI UNITED IMAGING HEALTHCARE CO., LTD., Shanghai (CN)

(72) Inventors: Wei Li, Shanghai (CN); Yongqin Xiao, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 176 days.

(21) Appl. No.: 18/057,734

(22) Filed: Nov. 21, 2022

(65) Prior Publication Data

US 2023/0083704 A1   Mar. 16, 2023

Related U.S. Application Data

(63) Continuation of application No. 17/105,643, filed on Nov. 27, 2020, now Pat. No. 11,504,083, which is a
(Continued)

(30) Foreign Application Priority Data

May 28, 2018   (CN) .......................... 201810525559.4
Oct. 31, 2018   (CN) .......................... 201811287450.8

(51) Int. Cl.
*A61B 6/00*   (2024.01)
*A61B 6/04*   (2006.01)
*A61B 6/46*   (2024.01)

(52) U.S. Cl.
CPC ................ *A61B 6/544* (2013.01); *A61B 6/04* (2013.01); *A61B 6/463* (2013.01)

(58) Field of Classification Search
CPC ........... A61B 6/544; A61B 6/04; A61B 6/463; A61B 6/032; A61B 6/545; A61B 6/5294; A61B 5/055; A61B 6/00; A61B 6/547
See application file for complete search history.

(56) References Cited

U.S. PATENT DOCUMENTS

| | | |
|---|---|---|
| 5,722,999 A | 3/1998 | Snell |
| 2002/0198447 A1 | 12/2002 | Van Muiswinkel et al. |

(Continued)

FOREIGN PATENT DOCUMENTS

| | | |
|---|---|---|
| CN | 101627917 A | 1/2010 |
| CN | 101721227 A | 6/2010 |

(Continued)

OTHER PUBLICATIONS

International Search Report in PCT/CN2019/088886 mailed on Aug. 28, 2019, 5 pages.
(Continued)

*Primary Examiner* — Courtney D Thomas
(74) *Attorney, Agent, or Firm* — METIS IP LLC

(57) ABSTRACT

Systems and methods for determining one or more target examination parameters is provided. The methods may include obtaining target examination information of a subject and generating one or more initial examination parameters based on the target examination information. The methods may further include obtaining one or more historical examination parameters associated with the subject and updating at least one of the one or more initial examination parameters based on the one or more historical examination parameters to obtain one or more target examination parameters. The one or more target examination parameters may be used for performing a target examination on the subject.

19 Claims, 11 Drawing Sheets

Related U.S. Application Data continuation of application No. PCT/CN2019/088886, filed on May 28, 2019.

(56) References Cited

U.S. PATENT DOCUMENTS

| | | |
|---|---|---|
| 2007/0053503 A1 | 3/2007 | Zelnik et al. |
| 2012/0027174 A1 | 2/2012 | Takamura |
| 2013/0083894 A1 | 4/2013 | Niebler et al. |
| 2015/0073255 A1 | 3/2015 | Liu et al. |
| 2016/0015331 A1 | 1/2016 | Wullenweber |
| 2016/0042012 A1 | 2/2016 | Lou et al. |
| 2016/0183905 A1 | 6/2016 | Lou et al. |
| 2017/0249423 A1 | 8/2017 | Wang et al. |
| 2017/0329903 A1* | 11/2017 | Shu .................. G06F 16/51 |

FOREIGN PATENT DOCUMENTS

| | | |
|---|---|---|
| CN | 103284733 A | 9/2013 |
| CN | 103340646 A | 10/2013 |
| CN | 103383701 A | 11/2013 |
| CN | 105615912 A | 6/2016 |
| CN | 107122605 A | 9/2017 |
| CN | 107320124 A | 11/2017 |
| CN | 107802265 A | 3/2018 |
| CN | 108652654 A | 10/2018 |
| CN | 108670279 A | 10/2018 |
| CN | 109524102 A | 3/2019 |

OTHER PUBLICATIONS

Written Opinion in PCT/CN2019/088886 mailed on Aug. 28, 2019, 5 pages.
First Office Action in Chinese Application No. 201810525559.4 mailed on Jul. 29, 2019, 23 pages.
First Office Action in Chinese Application No. 201811287450.8 mailed on Mar. 25, 2020, 18 pages.
The Fourth Office Action in Chinese Application No. 201810525559.4 mailed on Apr. 2, 2021, 27 pages.
The Extended European Search Report in European Application No. 19811874.7 mailed on May 17, 2021, 8 pages.

* cited by examiner

SYSTEMS AND METHODS FOR DETERMINING EXAMINATION PARAMETERS

CROSS-REFERENCE TO RELATED APPLICATIONS

This application is a continuation of U.S. patent application Ser. No. 17/105,643, filed on Nov. 27, 2020, which is a continuation of International Patent Application No. PCT/CN2019/088886, filed on May 28, 2019, which claims priority to Chinese Application No. 201810525559.4, filed on May 28, 2018, and Chinese Application No. 201811287450.8, filed on Oct. 31, 2018, and the entire contents of each of the above related applications are hereby incorporated by reference.

TECHNICAL FIELD

The present disclosure generally relates to the field of medical technology, and more particularly, relates to systems and methods for determining one or more target examination parameters for a target examination to be performed on a subject.

BACKGROUND

Before an examination is performed on a subject (e.g., a patient), the subject usually needs to provide examination information such as the name, the age, the gender, a type of the examination, a target portion of the subject to be examined, etc. A user (e.g., an operator or a doctor) can determine one or more examination parameters for the examination to be performed on the subject. In some cases, the one or more parameters can be unsuitable for the examination to be performed on the subject. The user may sometimes need to correct at least one of the one or more examination parameters and perform the examination on the subject again. The examination may be, for example, a medical examination such as a scan on the subject using an imaging device. To perform the scan on the target portion of the subject, the user often needs to position the subject in the imaging device and determine a target region (i.e., an examination parameter) that includes the target portion of the subject to be scanned using a laser indicator or a radiation field indicator of a beam limiter. This may cause inconvenience to the subject and/or increase the workload of the user. Therefore, it is desired to provide systems and methods for more accurately and efficiently determine one or more examination parameters for an examination on a subject.

SUMMARY

According to an aspect of the present disclosure, a method is provided. The method may be implemented on a computing device having at least one processor and at least one non-transitory storage medium. The method may include obtaining height data of a subject. The method may further include determining, based on the height data of the subject, a target region corresponding to a target portion of the subject for a scan on the subject by an imaging device. The target portion may be within the target region. The method may further include determining, based on the target region, a plurality of movement parameters associated with the imaging device. The plurality of movement parameters may include at least one start position and at least one end position associated with one or more components of the imaging device.

In some embodiments, the determining, based on the height data of the subject, a target region corresponding to a target portion of the subject to be scanned by an imaging device may include obtaining a database including a plurality of datasets, wherein each of the plurality of datasets may include height data and a plurality of candidate regions corresponding to a plurality of candidate portions associated with a plurality of candidate height data; determining one or more target datasets from the plurality of datasets, wherein the height data in the one or more target datasets is closest, among the plurality of datasets, to the height data of the subject; and determining the target region based on one or more candidate regions in the one or more target datasets that correspond to the target portion.

In some embodiments, the method may further include determining that the height data of multiple target datasets, among the plurality of datasets, is closest to the height data of the subject. The determining the target region based on one or more candidate regions in the one or more target datasets that correspond to the target portion may include identifying, in the multiple target datasets, multiple candidate regions corresponding to the target portion; and determining, based on the multiple candidate regions corresponding to the target portion, an average region as the target region.

In some embodiments, the method may further include determining a difference between the height data in the one or more target datasets and the height data of the subject; comparing the difference with a threshold; and in response to a determination that the difference is greater than the threshold, correcting the target region.

In some embodiments, the method may further include storing the height data of the subject and the target region corresponding to the target portion of the subject in the database.

In some embodiments, the method may further include comparing a size of the target region and a size of a maximum scanning range of a single scan by the imaging device; and in response to a result that the size of the target region is greater than the size of the maximum scanning range of a single scan by the imaging device, causing the imaging device to perform, based on the plurality of movement parameters, a plurality of sub-scans on the target portion to obtain a plurality of images, wherein the plurality of movement parameters include a plurality of start positions corresponding to the plurality of sub-scans and a plurality of end positions corresponding to the plurality of sub-scans; and generating a panoramic image by stitching the plurality of images.

In some embodiments, the method further include causing one or more components of the imaging device to move according to the plurality of movement parameters to obtain a simulated region to be scanned on the subject and determining whether the simulated region matches the target portion of the subject. The method may further include in response to a determination that the simulated region does not match the target portion of the subject, correcting at least one of the plurality of movement parameters.

In some embodiments, the method may further include identifying the simulated region using at least one of a laser indicator or a radiation field indicator of a beam limiter.

In some embodiments, the determining, based on the target region, a plurality of movement parameters associated with the imaging device may include determining a position of the subject in the imaging device, and determining the plurality of movement parameters based on the target region and the position of the subject in the imaging device.

According to another aspect of the present disclosure, a system is provided. The system may include at least one non-transitory storage medium including a set of instructions and at least one processor in communication with the at least one non-transitory storage medium. When executing the set of instructions, the at least one processor may be directed to cause the system to obtain height data of a subject. The at least one processor may be further directed to cause the system to determine, based on the height data of the subject, a target region corresponding to a target portion of the subject for a scan on the subject by an imaging device. The target portion may be within the target region. The at least one processor may be further directed to cause the system to determine, based on the target region, a plurality of movement parameters associated with the imaging device. The plurality of movement parameters may include at least one start position and at least one end position associated with one or more components of the imaging device.

According to yet another aspect of the present disclosure, a system is provided. The system may include an obtaining module, configured to obtain height data of a subject. The system may further include a determination module, configured to determine, based on the height data of the subject, a target region corresponding to a target portion of the subject for a scan on the subject by an imaging device. The target portion may be within the target region. The system may further include a scanning module, configured to determine, based on the target region, a plurality of movement parameters associated with the imaging device. The plurality of movement parameters may include at least one start position and at least one end position associated with one or more components of the imaging device.

According to still another aspect of the present disclosure, a non-transitory computer readable medium is provided. The non-transitory computer readable medium may include at least one set of instructions. When executed by at least one processor of a computing device, the at least one set of instructions may direct the at least one processor to obtain a database including a plurality of datasets. Each of the plurality of datasets may include height data and a plurality of candidate regions corresponding to a plurality of candidate portions associated with a plurality of candidate height data. The at least one set of instructions may further direct the at least one processor to determine one or more target datasets from the plurality of datasets. The height data in the one or more target datasets may be closest, among the plurality of datasets, to the height data of the subject. The at least one set of instructions may further direct the at least one processor to determine the target region based on one or more candidate regions in the one or more target datasets that correspond to the target portion.

According to yet another aspect of the present disclosure, a method for determining one or more target examination parameters is provided. The method may be implemented on a computing device having at least one processor and at least one non-transitory storage medium. The method may include obtaining target examination information of a subject and generating one or more initial examination parameters based on the target examination information. The method may further include obtaining one or more historical examination parameters associated with the subject and updating at least one of the one or more initial examination parameters based on the one or more historical examination parameters to obtain one or more target examination parameters. The one or more target examination parameters may be used for performing a target examination on the subject.

In some embodiments, the obtaining one or more historical examination parameters of the subject may include obtaining one or more first historical examination records associated with the subject; determining whether the one or more first historical examination records include one or more second historical examination records matching the target examination information; and in response to a determination that the one or more first historical examination records include one or more second historical examination records matching the target examination information, obtaining the one or more historical examination parameters from the one or more second historical examination records.

In some embodiments, the obtaining the one or more historical examination parameters from the one or more second historical examination records may include determining whether only one second historical examination record matches the target examination information; and in response to a determination that only one second historical examination record matches the target examination information, obtaining the one or more historical examination parameters from the only one second historical examination record.

In some embodiments, the obtaining the one or more historical examination parameters from the one or more second historical examination records may include assessing, for each of the one or more second historical examination records, a degree of similarity between examination information of an examination corresponding to the second historical examination record and the target examination information; identifying, from the one or more second historical examination records, a third historical examination record of an examination that has, among the one or more second historical examination records, a highest degree of similarity with the target examination information; and obtaining the one or more historical examination parameters from the third historical examination record.

In some embodiments, the assessing, for each of the one or more second historical examination records, a degree of similarity between examination information of an examination corresponding to the second historical examination record and the target examination information may include comparing, for each of the one or more second historical examination records, a time when an examination corresponding to the second historical examination record occurred and a time of the target examination. The identifying a third historical examination record of an examination that has, among the one or more second historical examination records, a highest degree of similarity with the target examination information may include designating a second historical examination record of an examination that, among the one or more second historical examination records, occurred at a time closest to the time of the target examination as the third historical examination record.

In some embodiments, the assessing, for each of the one or more second historical examination records, a degree of similarity between examination information of an examination corresponding to the second historical examination record and the target examination information may include comparing, for each of the one or more second historical examination records, a parameter of interest of a device used in an examination corresponding to the second historical examination record and a corresponding parameter of a device to be used in the target examination.

In some embodiments, the comparing, for each of the one or more second historical examination records, a parameter of interest of a device used in an examination corresponding to the second historical examination record and a corresponding parameter of a device to be used in the target examination may include determining that for each examination that corresponds to one of the one or more second historical examination records, the parameter of interest of a device used therein is different from the corresponding parameter of the device to be used in the target examination; and in response to a determination that for each examination that corresponds to one of the one or more second historical examination records, the parameter of interest of a device used therein is different from the corresponding parameter of the device to be used in the target examination, comparing a time when each of one or more examinations corresponding to the one or more second historical examination records occurred and a time of the target examination. The identifying a third historical examination record of an examination that has, among the one or more second historical examination records, a highest degree of similarity with the target examination information may include designating a second historical examination record of an examination that, among the one or more second historical examination records, occurred at a time closest to the time of the target examination as the third historical examination record.

In some embodiments, the comparing a parameter of interest of a device used in an examination corresponding to each of the one or more second historical examination records and a corresponding parameter of a device to be used in the target examination may include determining that the parameter of interest of a device used in only one examination corresponding to one of the one or more second historical examination records is the same as the corresponding parameter of the device to be used in the target examination. The identifying a third historical examination record of an examination that has, among the one or more second historical examination records, a highest degree of similarity with the target examination information may include designating a second historical examination record corresponding to the only examination using the device whose parameter of interest is the same as the corresponding parameter of the device to be used in the target examination as the third historical examination record.

In some embodiments, the comparing a parameter of interest of a device used in an examination corresponding to each of the one or more second historical examination records and a corresponding parameter of a device to be used in the target examination may include determining that for each of more than one examination that corresponds to more than one second historical examination record of the one or more second historical examination records, the parameter of interest of a device used therein is the same as the corresponding parameter of the device to be used in the target examination; and in response to a determination that for each of more than one examination that corresponds to more than one second historical examination of the one or more second historical examination records, the parameter of interest of a device used therein is the same as the corresponding parameter of the device to be used in the target examination, comparing a time when each of the more than one examination occurred and a time of the target examination. The identifying a third historical examination record of an examination that has, among the one or more second historical examination records, a highest degree of similarity with the target examination information may include designating a second historical examination record of an examination that, among the more than one second historical examination record corresponding to the more than one examination each using a device whose parameter of interest is the same as the corresponding parameter of the device to be used in the target examination, occurred at a time closest to the time of the target examination as the third historical examination record.

In some embodiments, the comparing, for each of the one or more second historical examination records, a parameter of interest of a device used in an examination corresponding to the second historical examination record and a corresponding parameter of a device to be used in the target examination may include determining that, for each of more than one examination that corresponds to more than one second historical examination record of the one or more second historical examination records, the parameter of interest of a device used therein is the same as the corresponding parameter of the device to be used in the target examination; and in response to a determination that for each of more than one examination that corresponds to more than one second historical examination record of the one or more second historical examination records, the parameter of interest of a device used therein is the same as the corresponding parameter of the device to be used in the target examination, comparing, for each of the more than one examination, at least one position parameter associated with the examination and at least one position parameter associated with the subject to be used in the target examination. The identifying a third historical examination record of an examination that has, among the one or more second historical examination records, a highest degree of similarity with the target examination information may include determining whether for only one examination among the more than one examination each using the device whose parameter of interest is the same as the corresponding parameter of the device to be used in the target examination, at least one position parameter associated with the subject used therein is the same as the at least one position parameter associated with the subject to be used in the target examination; and in response to a determination that for only one examination among the more than one examination each using the device whose parameter of interest is the same as the corresponding parameter of the device to be used in the target examination, at least one position parameter associated with the subject used therein is the same as the at least one position parameter associated with the subject to be used in the target examination, designating a second historical examination record corresponding to the only one examination as the third historical examination record.

In some embodiments, the comparing, for each of the one or more second historical examination records, a parameter of interest of a device used in an examination corresponding to the second historical examination record and a corresponding parameter of a device to be used in the target examination may include determining that for each of more than one examination that corresponds to more than one second historical examination of the one or more second historical examination records, the parameter of interest of a device used therein is the same as the corresponding parameter of the device to be used in the target examination; and in response to a determination that for each of more than one examination that corresponds to more than one second historical examination of the one or more second historical examination records, the parameter of interest of a device used therein is the same as the corresponding parameter of the device to be used in the target examination, comparing at least one position parameter associated with the subject in the more than one examination and at least one position parameter associated with the subject in the target examination. The identifying a third historical examination record of an examination that has, among the one or more second historical examination records, a highest degree of similarity with the target examination information may include determining whether for each of multiple examinations among the more than one examination each using a device whose parameter of interest is the same as the corresponding parameter of the device to be used in the target examination, at least one position parameter associated with the subject used therein is the same as the at least one position parameter associated with the subject to be used in the target examination; and in response to a determination that for each of multiple examinations among the more than one examination each using a device whose parameter of interest is the same as the corresponding parameter of the device to be used in the target examination, at least one position parameter associated with the subject used therein is the same as the at least one position parameter associated with the subject to be used in the target examination, comparing a time when each of the multiple examinations occurred and a time of the target examination, and designating a second historical examination record of an examination that, among the multiple examinations each using a device whose parameter of interest is the same as the corresponding parameter of the device to be used in the target examination and having at least one position parameter associated with the subject that is the same as the at least one position parameter associated with the subject to be used in the target examination, occurred at a time closest to the time of the target examination as the third historical examination record.

In some embodiments, the comparing, for each of the one or more second historical examination records, a parameter of interest of a device used in an examination corresponding to the second historical examination record and a corresponding parameter of a device to be used in the target examination may include determining that for each of more than one examination that corresponds to more than one of the one or more second historical examination records, the parameter of interest of a device used therein is the same as the corresponding parameter of the device to be used in the target examination; and in response to a determination that for each of more than one examination that corresponds to more than one of the one or more second historical examination records, the parameter of interest of a device used therein is the same as the corresponding parameter of the device to be used in the target examination, comparing at least one position parameter associated with the subject in the more than one examination and at least one position parameter associated with the subject in the target examination. The identifying a third historical examination record of an examination that has, among the one or more second historical examination records, a highest degree of similarity with the target examination information may include determining whether for each examination of the more than one examination each using a device whose parameter of interest is the same as the corresponding parameter of the device to be used in the target examination, at least one position parameter associated with the subject used therein is different from the at least one position parameter associated with the subject to be used in the target examination; and in response to a determination that for each examination of the more than one examination each using a device whose parameter of interest is the same as the corresponding parameter of the device to be used in the target examination, at least one position parameter associated with the subject used therein is different from the at least one position parameter associated with the subject to be used in the target examination, comparing a time when each of the multiple examinations occurred and a time of the target examination, and designating a second historical examination record of an examination that, among the more than one second historical examination record corresponding to the more than one examination each using a device whose parameter of interest is the same as the corresponding parameter of the device to be used in the target examination, occurred at a time closest to the time of the target examination as the third historical examination record.

In some embodiments, the parameter of interest of the device may include a device model.

In some embodiments, the method may further include storing the one or more examination parameters of the target examination of the subject.

In some embodiments, the computing device may include a data recorder.

In some embodiments, the target examination may be a scan on the subject by an imaging device. The target examination information of the subject may include height data and a target portion of the subject to be scanned by the imaging device. The one or more target examination parameters may include a target region corresponding to the target portion of the subject. The target portion may be within the target region.

In some embodiments, the method may further include determining, based on the target region, a plurality of movement parameters associated with the imaging device, wherein the plurality of movement parameters include at least one start position and at least one end position associated with one or more components of the imaging device.

In some embodiments, the determining, based on the target region, a plurality of movement parameters associated with the imaging device may include determining a position of the subject in the imaging device; and determining the plurality of movement parameters based on the target region and the position of the subject in the imaging device.

According to still another aspect of the present disclosure, a system for determining one or more target examination parameters is provided. The system may include at least one non-transitory storage medium including a set of instructions and at least one processor in communication with the at least one non-transitory storage medium. When executing the set of instructions, the at least one processor may be directed to cause the system to obtain target examination information of a subject and generate one or more initial examination parameters based on the target examination information. The at least one processor may be further directed to cause the system to obtain one or more historical examination parameters associated with the subject and update at least one of the one or more initial examination parameters based on the one or more historical examination parameters to obtain one or more target examination parameters, wherein the one or more target examination parameters are used for performing a target examination on the subject.

According to yet another aspect of the present disclosure, a system for determining one or more target examination parameters is provided. The system may include an acquisition module, configured to obtain target examination information of a subject and obtain one or more historical examination parameters associated with the subject. The system may further include a parameter generation module, configured to generate one or more initial examination parameters based on the target examination information. The system may further include a parameter updating module, configured to update at least one of the one or more initial examination parameters based on the one or more historical examination parameters to obtain one or more target examination parameters. The one or more target examination parameters may be used for performing a target examination on the subject.

According to still another aspect of the present disclosure, a non-transitory computer readable medium is provided. The non-transitory computer readable medium may include at least one set of instructions for determining one or more target examination parameters. When executed by at least one processor of a computing device, the at least one set of instructions may direct the at least one processor to obtain target examination information of a subject; generate one or more initial examination parameters based on the target examination information; obtain one or more historical examination parameters associated with the subject; and update at least one of the one or more initial examination parameters based on the one or more historical examination parameters to obtain one or more target examination parameters, wherein the one or more target examination parameters are used for performing a target examination on the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts.

Figure 2:
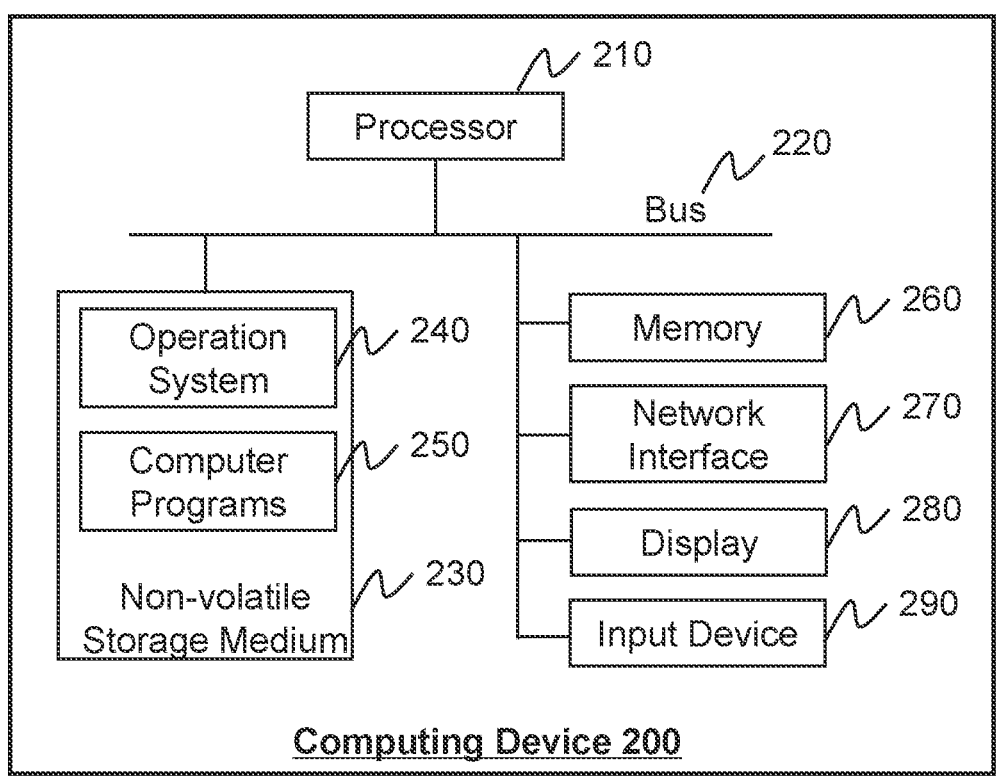
FIG. 2 is a schematic diagram illustrating exemplary hardware and/or software components of an exemplary computing device according to some embodiments of the present disclosure.

Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, an X-ray imaging system, a computed tomography (CT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a digital subtraction angiography-magnetic resonance imaging (DSA-MRI) system, etc. It should be noted that the imaging system described below is merely provided for illustration purposes, and not intended to limit the scope of the present disclosure.

According to an aspect of the present disclosure, mechanisms (which can include methods, systems, a computer-readable medium, etc.) for determining a plurality of movement parameters associated with an imaging device for a scan on a subject is provided. For example, height data of the subject may be obtained. A target region corresponding to a target portion of the subject for the scan may be determined based on the height data. A plurality of datasets may be obtained. Each of the plurality of datasets may include height data and a plurality of candidate regions corresponding to a plurality of candidate portions associated with the candidate height data. One or more target datasets may be determined from a plurality of datasets stored in a database. The height data in the one or more target datasets may be closest, among the plurality of datasets, to the height data of the subject. The target region may be determined based on one or more candidate regions in the one or more target datasets. The plurality of movement parameters may be determined based on the target region. The plurality of movement parameters may include at least one start location and at least one end location associated with one or more components of the imaging device, such as a couch or a gantry. The method for determining the plurality of movement parameters as described in the present disclosure is relatively simple and fast. Since the target region may be determined automatically, the operation process of a user such as a doctor or an operator may be simplified, and the time needed for the scan may be reduced.

According to another aspect of the present disclosure, mechanisms (which can include methods, systems, a computer-readable medium, etc.) for determining one or more target examination parameters for a target examination to be performed on a subject are provided. The method may include obtaining target examination information of the subject. The target examination information may include, for example, the name, the age, the gender, a type of the target examination, a target portion of the subject to be examined, etc. A plurality of initial examination parameters may be determined for the target examination. The one or more target examination parameters may be obtained by updating the plurality of initial examination parameters by updating at least one of the one or more initial examination parameters based on one or more historical examination parameters. The one or more historical examination parameters may be obtained from one of the historical examination records of the subject that matches the target examination information. The method for determining the one or more target examination parameters as described in the present disclosure may improve an accuracy of the one or more target examination parameters for the subject. Since the one or more target parameters are determined based on a historical examination record of the subject, the one or more target examination parameters may be more suitable for the subject. In some cases, the target examination may be a scan on the target portion of the subject using an imaging device. The target examination information of the subject may include height data of the subject and a target portion (e.g., a lung, a leg) of the subject. The one or more target examination parameters may include a target region of the subject to be scanned by the imaging device. The target portion may be within the target region. Since the target region can be automatically determined based on a historical examination record of the subject, the target region may be more accurate. The workload of the operator or the doctor may also be decreased.

Figure 1:
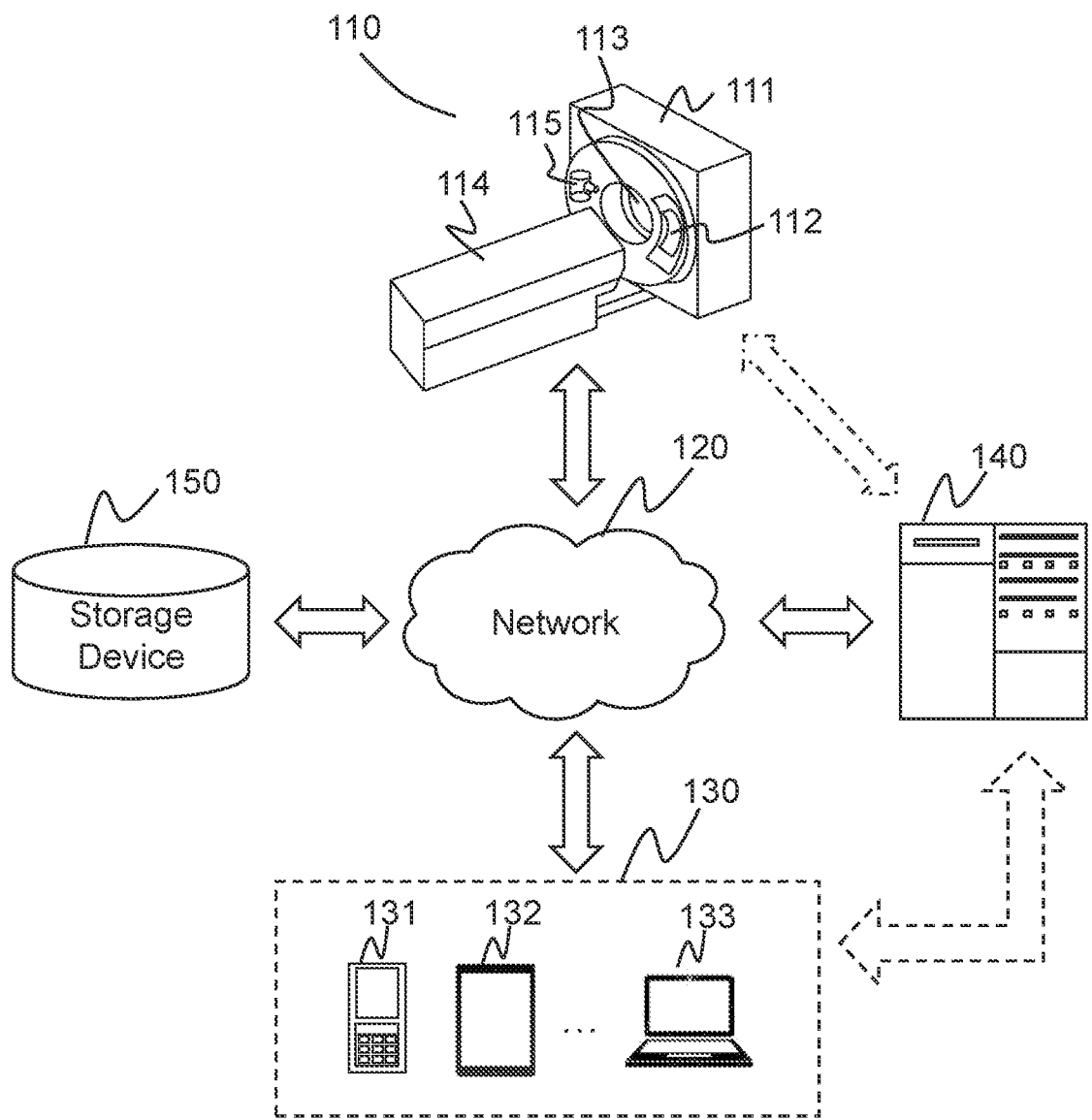
FIG. 1 is a schematic diagram illustrating an exemplary system for performing a target examination on a subject according to some embodiments of the present disclosure.

FIG. 1 is a schematic diagram illustrating an exemplary system for performing a target examination on a subject according to some embodiments of the present disclosure. As shown, the system 100 may include a device 110 for performing a target examination on the subject, a network 120, one or more terminals 130, a processing device 140, and a storage device 150. In some embodiments, the device 110, the terminal(s) 130, the processing device 140, and/or the storage device 150 may be connected to and/or communicate with each other via a wireless connection (e.g., the network 120), a wired connection, or a combination thereof. The connection between the components of the system 100 may be variable. Merely by way of example, the device 110 may be connected to the processing device 140 through the network 120, as illustrated in FIG. 1. As another example, the device 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The device 110 may perform a target examination on a subject (e.g., a patient). For example, the target examination may be a medical examination. The device 110 may be an imaging device for performing a scan on a target portion (e.g., a lung, a liver) of the subject. As another example, the device may be an electrocardiograph for determining electrocardio signals of the heart of the subject. In some embodiments, the imaging device 110 may include a single-modality scanner and/or a multi-modality scanner. The single-modality scanner may include, for example, a computed tomography (CT) scanner, a magnetic resonance (MR) scanner, an ultrasonoscope, a positron emission tomography (PET) scanner, etc. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the subject may include a body, a substance, an object, or the like, or a combination thereof. In some embodiments, the target portion of the subject to be scanned may include the head, the thorax, the abdomen, or the like, or a combination thereof.

In some embodiments, the device 110 may include a gantry 111, a detector 112, a detecting region 113, a scanning table 114, and a radiation source 115. The gantry 111 may support the detector 112 and the radiation source 115. A subject may be placed on the scanning table 114 to be scanned. The radiation source 115 may emit radiation beams to the subject. The radiation may include a particle ray, a photon ray, or the like, or a combination thereof. In some embodiments, the radiation beams may include a plurality of radiation particles (e.g., neutrons, protons, electron, p-mesons, heavy ions), a plurality of radiation photons (e.g., X-ray, a y-ray, ultraviolet, laser), or the like, or a combination thereof. The detector 112 may detect radiation beams and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

Figure 7:
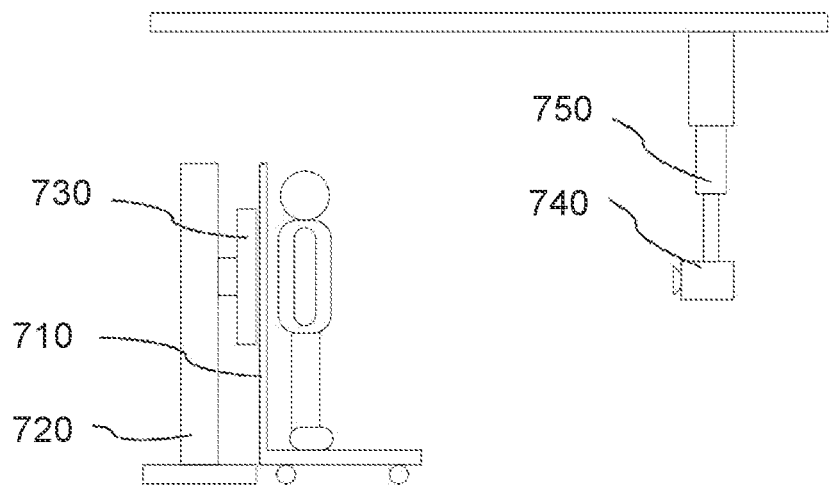
FIG. 7 is a schematic diagram illustrating an exemplary X-ray machine according to some embodiments of the present disclosure.

In some embodiments, the device 110 may be integrated with one or more other devices that may facilitate the scanning of the subject, such as, an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner) that records the spatial representation of the subject. It should be noted that the structure of the device 110 shown in FIG. 1 is only for illustration purposes. For example, the device 110 may be an X-ray machine as shown in FIG. 7.

The network 120 may include any suitable network that can facilitate exchange of information and/or data for the system 100. In some embodiments, one or more components of the system 100 (e.g., the device 110, the processing device 140, the storage device 150, the terminal(s) 130) may communicate information and/or data with one or more other components of the system 100 via the network 120. For example, the processing device 140 may obtain image data from the device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the system 100 may be connected to the network 120 to exchange data and/or information.

The terminal(s) 130 may be connected to and/or communicate with the device 110, the processing device 140, and/or the storage device 150. For example, the terminal(s) 130 may obtain one or more target examination parameters of the target examination to be performed on the subject from the processing device 140. In some embodiments, the terminal(s) 130 may be part of the processing device 140. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof.

In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, interactions between the user and the system 100 may be implemented via the terminal(s) 130. For example, the user may give an instruction to one or more components of the system 100 via a user interface on the terminal(s) 130. The instruction may include directing the processing device 140 to start determining one or more target examination parameters for the target examination, directing the device 110 to start to perform the target examination on the subject according to the one or more target examination parameters for the target examination, etc. As another example, the terminal(s) 130 may present information to the user via the user interface, such as the one or more target examination parameters determined by the processing device 140, examination data obtained by the device 110, etc.

The processing device 140 may process data and/or information obtained from the device 110, the storage device 150, the terminal(s) 130, or other components of the system 100. For example, the processing device 140 may obtain examination information of the one or more historical examination records of the subject. The processing device 140 may determine one or more initial examination parameters for the target examination on the subject. The processing device 140 may update at least one of the one or more initial examination parameters to obtain one or more target examination parameters for the target examination on the subject. As another example, the processing device 140 may obtain height data of the subject. The processing device 140 may determine, based on the height data, a target region corresponding to a target portion of the subject for a scan on the subject by the device 110 (e.g., an imaging device). The processing device 140 may further determine a plurality of movement parameters associated with the imaging device.

In some embodiments, the processing device 140 may be a single server or a server group. The server group may be centralized or distributed. In some embodiments, the processing device 140 may be local to or remote from the system 100. For example, the processing device 140 may access information and/or data from the device 110, the storage device 150, and/or the terminal(s) 130 via the network 120. As another example, the processing device 140 may be directly connected to the device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the processing device 140, the terminal(s) 130, and/or the device 110. For example, the storage device 150 may store the target examination information of the subject and the one or more target examination parameters corresponding to the target examination information. As another example, the storage device 150 may store the height data of the subject and the target region corresponding to the target portion of the subject. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the system 100 (e.g., the processing device 140, the terminal(s) 130). One or more components of the system 100 may access the data or instructions stored in the storage device 150 via the network 120. In some embodiments, the storage device 150 may be part of the processing device 140.

The above description for FIG. 1 is intended to be illustrative and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200 shown in FIG. 2. For example, the computing device 200 may be a data recorder. The computing device 200 may include a processor 210, a non-volatile storage medium 230, a network interface 270, a display 280, and an input device 290 connected through a bus 220. The processor 210 of the computing device 200 may be have computing and controlling capabilities. The computing device 200 may include a non-volatile storage medium 230 and a memory 260. The non-volatile storage medium 230 may store an operation system 240 and computer programs 250. The memory 260 may be used for the operation of the operation system 240 and the computer programs 250 stored in the non-volatile storage medium 230. The computing device 200 may communicate with an external device (e.g., through the network interface 270. The computer program may be executed by the processor 210 to implement a method for determining one or more target examination parameters for a target examination on the subject. The display 280 of the computing device 200 may be a liquid crystal display or an electronic ink display. The input device of the computing device 200 may be a touch layer disposed on the display 280, a button, a trajectory ball, or a touchpad provided on an external housing of the computing device 200. As another example, the input device may be an external keyboard, a touchpad or a mouse.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the device 110, the terminals 130, the storage device 150, and/or any other component of the system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

In some embodiments, the storage may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure. For example, the storage may store a program for the processing device 140 for determining one or more target examination parameters of a target examination to be performed on the subject.

The network interface 270 may be connected to a network (e.g., the network 120) to facilitate data communications. For example, the network interface 270 may establish connections between the processing device 140 and the device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the network interface 270 may be and/or include a standardized communication port, such as RS232, RS485, etc. In some embodiments, the network interface 270 may be a specially designed communication port. For example, the network interface 270 may be designed in accordance with the digital imaging and communications in medicine (DICOM) protocol.

It will be understood by those skilled in the art that the structure shown in FIG. 2 is only provided for illustration purposes, which may not limit the computing device 200 on which the present disclosure is implemented. In some embodiments, the computing device 200 may include more or fewer components than the components shown in FIG. 2. In some embodiments, one or more components shown in FIG. 2 may be combined into a single component.

Figure 3:
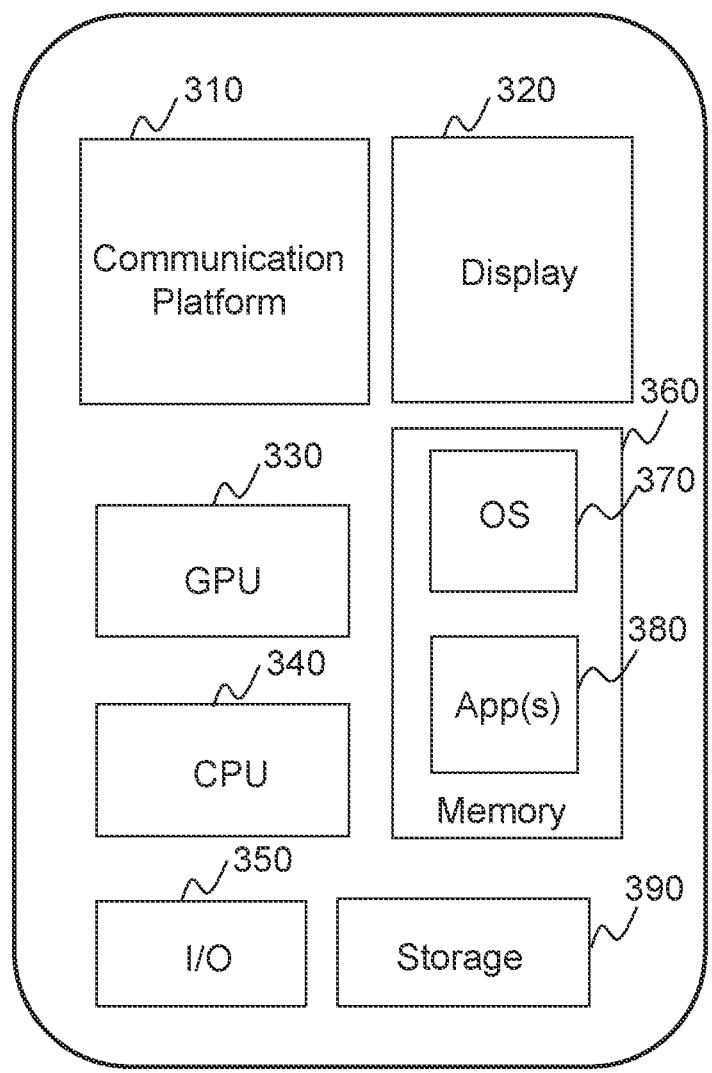
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal 130 may be implemented on the mobile device 300 shown in FIG. 3. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the determination of one or more target examination parameters or other information from the processing device 140. User interactions with the information stream may be achieved via the I/O 350 and provided to the processing device 140 and/or other components of the system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
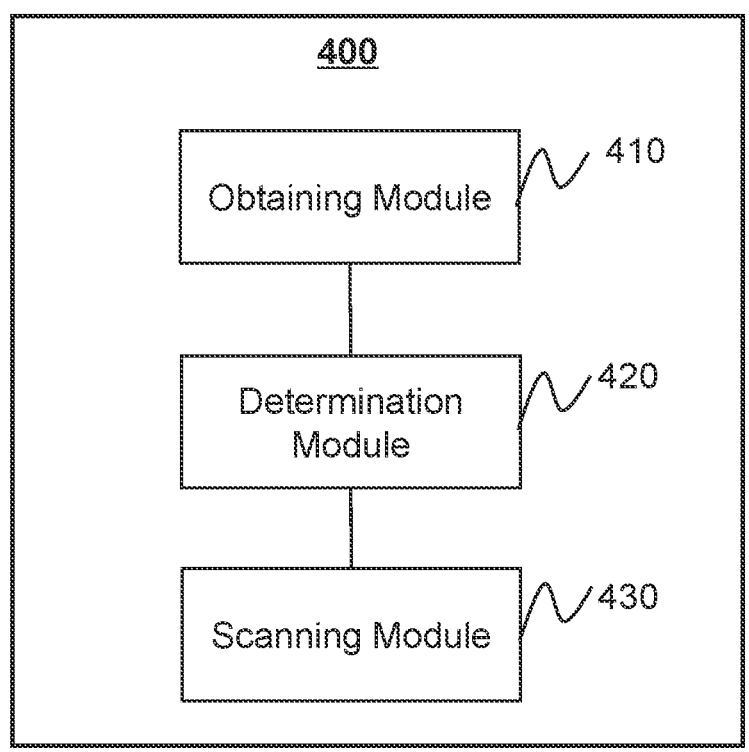
FIG. 4 is a block diagram illustrating an exemplary system for performing a scan on a subject according to some embodiments of the present disclosure.

FIG. 4 is a block diagram illustrating an exemplary system for performing a scan on a subject according to some embodiments of the present disclosure. As illustrated in FIG. 4, the system 400 may include an obtaining module 410, a determination module 420, and a scanning module 430. In some embodiments, at least a part of the system 400 may be implemented on the processing device 140. The modules may be hardware circuits of all or part of the processing device 140. The modules may also be implemented as an application or a set of instructions read and executed by the processing device 140. Further, the modules may be any combination of the hardware circuits and the application/ instructions. For example, the modules may be the part of the processing device 140 when the processing device 140 is executing the application/set of instructions.

The obtaining module 410 may obtain data from one or more components of the system 100, such as the storage device 150. In some embodiments, the obtaining module may obtain height data of a subject. The subject may include a biological subject (e.g., an animal, a human) or a non-biological subject (e.g., a phantom). In some embodiments, the height data of the subject may be obtained from a historical medical record of the subject stored in the storage device 150. Alternatively, when there is no historical medical record that includes the height data of the subject in the storage device 150, or when the subject is a child or a teenager whose height may increase as the subject grows older, a measurement of the height of the subject may be performed before the scan to obtain the height data of the subject. In some embodiments, the obtaining module 410 may obtain a database including a plurality of datasets corresponding to different height data. Each of the plurality of datasets may include height data and a plurality of candidate regions corresponding to a plurality of candidate portions associated with the height data. In some embodiments, the plurality of datasets may be determined based on a plurality of historical medical records or scientific research data of a plurality of subjects.

The determination module 420 may determine a target region based on the height data obtained by the obtaining module 410. The target region may correspond to a target portion of the subject to be scanned by an imaging device (e.g., the device 110). The determination module 420 may determine one or more target datasets from the plurality of datasets obtained by the obtaining module 410. The height data in the one or more target datasets may be closest, among the plurality of datasets, to the height data of the subject. The determination module 420 may further determine the target region based on one or more candidate regions in the one or more target datasets that correspond to the target portion of the subject.

The scanning module 430 may determine a plurality of movement parameters associated with the imaging device based on the target region. In some embodiments, one or more components of the imaging device may be controlled to move based on the plurality of movement parameters so that the scan can be performed on the target region of the subject. The one or more components of the imaging device may be moved before the scan and/or during the scan. For instance, when the imaging device is an X-ray machine, a mechanical arm connected to an X-ray generation device may be controlled to move the X-ray generation device, thereby directing X-rays towards the target region. As another example, when the imaging device is a cone beam CT scanner, a couch may be controlled to move, for example, along a horizontal direction to adjust the position of the subject respective to a radiation source, and a gantry where the radiation source is located may be controlled to rotate to adjust a direction of the radiation beams. If the one or more components of the imaging device is moved during the scan, the plurality of movement parameters may include a start location and an end location for the scan.

In some embodiments, the scanning module 430 may determine a position of the subject in the imaging device and determine the plurality of movement parameters based on the target region of the subject and the position of the subject in the imaging device. In some embodiments, the scanning module 430 may cause one or more components of the imaging device to move according to the plurality of movement parameters to obtain a simulated region to be scanned on the subject. The simulated region may be an actual region that the imaging device may scan. The scanning module 430 may determine whether the simulated region matches the target portion of the subject. In response to a determination that the simulated region does not match the target portion of the subject, the scanning module 430 may correct at least one of the one or more movement parameters so that the target portion of the subject may be scanned.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, any module mentioned above may be divided into two or more units. In some embodiments, the system 400 may include one or more additional modules. For example, the system 400 may further include a transmitting module configured to transmit the one or more movement parameters to the device 110. As another example, the system 400 may further include an imaging device (e.g., an X-ray machine).

Figure 5:
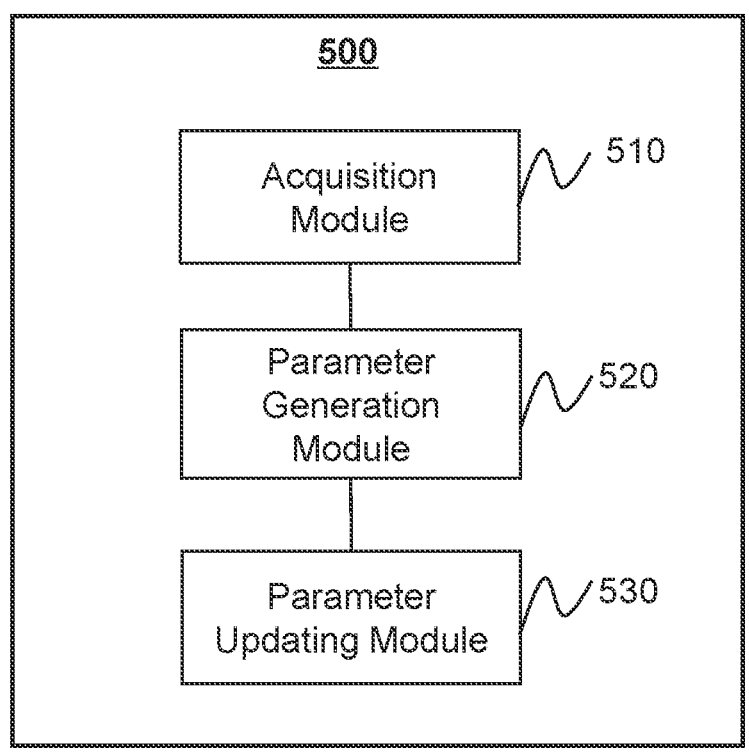
FIG. 5 is a block diagram illustrating an exemplary system for performing a target examination on a subject according to some embodiments of the present disclosure.

FIG. 5 is a block diagram illustrating an exemplary system for performing a target examination on a subject according to some embodiments of the present disclosure. As illustrated in FIG. 5, the device 500 may include an acquisition module 510, a parameter generation module 520, and a parameter updating module 530. In some embodiments, the device 500 may be implemented on the processing device 140. The modules may be hardware circuits of all or part of the processing device 140. The modules may also be implemented as an application or set of instructions read and executed by the processing device 140. Further, the modules may be any combination of the hardware circuits and the application/instructions. For example, the modules may be the part of the processing device 140 when the processing device 140 is executing the application/set of instructions.

The acquisition module 510 may obtain data from one or more components of the system 100, such as the storage device 150. Ins some embodiments, the acquisition module 510 may obtain target examination information of a subject. In some embodiments, the target examination information of the subject may include personal information of the subject, for example, the identification number, the name, the age, the gender, the height, the weight, or the like. Additionally or alternatively, the target examination information of the subject may further include a type of a target examination to be performed on the subject and/or a target portion of the subject to be examined such as a lung, a leg, the stomach, etc. In some embodiments, the target examination information of the subject may be obtained before the target examination is performed on the subject. In some embodiments, the acquisition module 510 may obtain one or more historical examination parameters associated with the subject. In some embodiments, the one or more historical examination parameters may correspond to the target examination information of the subject. The processing device 140 may obtain one or more first historical examination records associated with the subject. The one or more first historical examination records may correspond to different examination information of the subject. A doctor or an operator may have confirmed that the plurality of historical examination records of the subject can be used as a reference for the target examination.

The parameter generation module 520 may generate one or more initial examination parameters based on the target examination information. For instance, one or more examination parameters for a CT scan may include a tube voltage of a radiation source, a tube current of the radiation source, an irradiation field of a beam limiter, one or more position parameters related to the subject in the imaging device, a scanning mode (e.g., a helical scan, a non-helical scan), or the like, or any combination thereof. In some embodiments, there may be a plurality of sets of examination parameters corresponding to different target portions of the subject (e.g., a patient, an animal). The parameter generation module 520 and/or a user (e.g., an operator) may select a set of examination parameters from the plurality of sets of examination parameters according to a part of the subject's need to check. The selected set of examination parameters may be designated as the one or more initial examination parameters.

The parameter updating module 530 may update at least one of the one or more initial examination parameters based on the one or more historical examination parameters to obtain one or more target examination parameters. In some embodiments, the one or more historical examination parameters may be used as a reference for correcting at least one of the one or more initial examination parameters. In some embodiments, the one or more historical examination parameters may be used to replace at least one of the one or more initial examination parameters. In some embodiments, the parameter updating module 530 may automatically correct or replace the at least one of the one or more initial examination parameters based on the one or more historical examination parameters. In some embodiments, the operator may manually correct or replace the at least one of the one or more initial examination parameters based on the one or more historical examination parameters.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, at least a portion of the functions described for a module may be performed by another module. In some embodiments, a module described in FIG. 5 may be divided into one or more units. For example, the parameter generation module 520 may include a target examination information acquisition unit and a selecting unit. The target examination information acquisition unit, rather than the acquisition module 510, may obtain target examination information of the subject. The selecting unit may generate one or more initial examination parameters.

Figure 6:
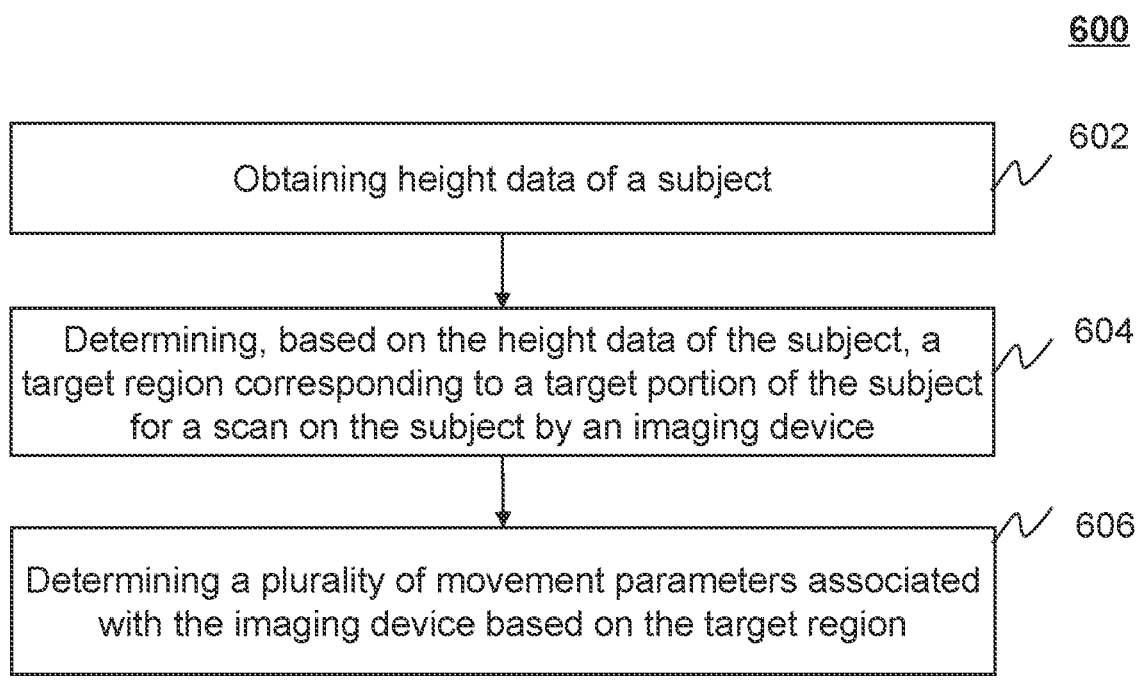
FIG. 6 is a flowchart illustrating an exemplary process for determining a plurality of movement parameters associated with an imaging device according to some embodiments of the present disclosure.

FIG. 6 is a flowchart illustrating an exemplary process for determining a plurality of movement parameters associated with an imaging device according to some embodiments of the present disclosure. At least a portion of process 600 may be implemented on the computing device 200 as illustrated in FIG. 2. In some embodiments, one or more operations of the process 600 may be implemented in the system 100 as illustrated in FIG. 1. The device 110 for performing an examination on a subject may be an imaging device for performing a scan on the subject. In some embodiments, one or more operations in the process 600 may be stored in the storage device 150 (e.g., the non-volatile storage medium 230, the memory 260, etc.) as a form of instructions, and invoked and/or executed by the processing device 140, the processor 210 of the computing device 200, and/or one or more modules in FIG. 4. In some embodiments, the instructions may be transmitted in the form of electronic current or electrical signals.

In 602, the processing device 140 (e.g., the obtaining module 410) may obtain height data of a subject. The subject may include a biological subject (e.g., an animal, a human) or a non-biological subject (e.g., a phantom). In some embodiments, the height data of the subject may be obtained from a historical medical record of the subject. As used herein, a historical medical record, or referred to as a historical examination record, of a subject may be a record of an examination of the subject performed previously. For example, when the subject is an adult human (e.g., between the age of 25 years old and 50 years old), the height of the subject may tend to remain unchanged as the subject grows older. Thus, the processing device 140 may obtain the height data of the subject from a historical medical record (e.g., a latest historical medical record) of the subject stored in the storage device 150. Alternatively, when there is no historical medical record that includes the height data of the subject in the storage device 150, or when the subject is a child or a teenager whose height may increase as the subject grows older, a measurement of the height of the subject may be performed before the scan to obtain the height data of the subject.

In 604, the processing device 140 (e.g., the determination module 420) may determine, based on the height data of the subject, a target region corresponding to a target portion of the subject for a scan on the subject by an imaging device. The target portion of the subject may include, for example, the head, the chest, the abdomen, a breast, a leg, or the like, or a portion thereof, or a combination thereof. In some embodiments, the target portion may be identified from a historical medical record (e.g., a latest historical medical record) of the subject. For instance, if the latest historical medical record indicates that the subject is suffering from a tumor located in the left lung and the scan is intended to obtain information related to the tumor, the processing device 140 may identify the target portion as the left lung. Alternatively, the target portion may be determined based on a manual input by a user, such as a doctor or an operator. As used herein, the term "target region" refers to a region of the subject that includes the target portion. The medical imaging device may perform the scan on the target region of the subject. For example, the scan may be an X-ray scan, a CT scan, an MR scan, a PET scan, or the like, or a combination thereof. In some embodiments, the scan may be a pre-scan for obtaining a scout image of the subject. The scout image may be used to locate a region of interest (ROI) within the target region for a subsequent scan. For instance, the ROI may include a tumor, a broken bone, calcified tissue, or the like, or any combination thereof.

For a subject such as a human or an animal, the location of different portions of the subject may be associated with a height of the subject. Thus, the target region to be scanned by the medical imaging device may correlate with the height data of the subject. For instance, the processing device 140 may obtain a database including a plurality of datasets corresponding to different height data. Each of the plurality of datasets may include height data and a plurality of candidate regions corresponding to a plurality of candidate portions associated with the height data. In some embodiments, the plurality of datasets may be determined based on a plurality of historical medical records or scientific research data of a plurality of subjects. In some embodiments, each of the plurality of candidate region corresponding to the height data and one of the plurality of candidate portions may be an average candidate region determined based on the plurality of historical medical records or the scientific research data. The processing device 140 may determine one or more target datasets from the plurality of datasets. The height data in the one or more target datasets may be closest, among the plurality of datasets, to the height data of the subject. The processing device 140 may further determine the target region based on one or more candidate regions in the one or more target datasets that correspond to the target portion of the subject. More details regarding the determination of the target region may be found elsewhere in the present disclosure, for example, in FIG. 8 and the description thereof.

In 606, the processing device 140 (e.g., the scanning module 430) may determine a plurality of movement parameters associated with the imaging device based on the target region. In some embodiments, one or more components of the imaging device may be controlled to move based on the plurality of movement parameters so that the scan can be performed on the target region of the subject. The one or more components of the imaging device may be moved before the scan and/or during the scan. For instance, when the imaging device is an X-ray machine, a mechanical arm connected to an X-ray generation device may be controlled to move the X-ray generation device, thereby directing X-rays towards the target region. As another example, when the imaging device is a cone beam CT scanner, a couch may be controlled to move, for example, along a horizontal direction to adjust the position of the subject respective to a radiation source, and a gantry where the radiation source is located may be controlled to rotate to adjust a direction of the radiation beams. If the one or more components of the imaging device is moved during the scan, the plurality of movement parameters may include a start location and an end location for the scan.

In some embodiments, the processing device 140 may determine a position of the subject in the imaging device and determine the plurality of movement parameters based on the target region of the subject and the position of the subject in the imaging device. The position of the subject in the imaging device may be a position of the subject relative to one or more components of the imaging device. For instance, the position of the subject in a CT scanner may be the position of the subject relative to a couch of the CT scanner. For instance, the plurality of movement parameters for the scan on the subject may include a set of movement parameters for each of the one or more components of the imaging device that is controlled to move for performing the scan, such as the mechanical arm of the X-ray machine, the couch or the gantry of the cone beam CT scanner, etc. In some embodiments, the processing device 140 may transmit the plurality of movement parameters to one or more components of the system 100, such as the device 110, the terminal 130, and/or the storage device 150. In some embodiments, the processing device 140 may determine the plurality of movement parameters associated with the imaging device for the scan and control the imaging device to perform the scan on the target region of the subject based on the plurality of movement parameters.

In some embodiments, the processing device 140 may compare a size of the target region and a size of a maximum scanning range of a single scan by the imaging device. In response to a result that the size of the target region is greater than the maximum scanning scope, the imaging device may perform a plurality of sub-scans on the target portion of the subject to obtain a panoramic image. For instance, when the scan is to be performed on a large target portion of the subject, such as the spine and/or the lower limbs of the subject, the maximum scanning range of the imaging device (e.g., the X-ray machine) may be smaller than the target region. A plurality of sub-regions may be generated based on the target region. In some embodiments, the plurality of sub-regions may be overlapped by each other. The imaging device may perform a plurality of sub-scans on the plurality of sub-regions to obtain a plurality of images. The movement parameters for each of the plurality of sub-scans may include a start position and an end location corresponding to one of the plurality of sub-regions. A plurality of images may be obtained by the plurality of sub-scans on the plurality of sub-regions.

The method for determining the plurality of movement parameters as described is relatively simple and fast, which may simplify the operation process of the doctor or the operator, reduce the time duration of the scan. The method may also avoid using a radiation field indicator of a beam limiter to determine the target region, thereby avoiding possible harm to the subject (e.g., a patient) caused by the radiation field indicator.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 600 may further include an operation to transmit the plurality of movement parameters to one or more components of the system 100, such as the terminal(s) 130 and/or the device 110.

FIG. 7 is a schematic diagram illustrating an exemplary X-ray generation device according to some embodiments of the present disclosure. The device 110 may be implemented on the device 700 shown in FIG. 7. The device 700 may include a support 710, a column 720, a panel detector 730 (e.g., a flat panel detector), an X-ray generation device 740, a mechanical arm 750, and a processor (e.g., the processing device 140 or the processor 210 of the computing device 200). The support 710 may be directed towards the X-ray generation device 740, and the X-ray generation device 740 may be connected with the mechanical arm 750 that is disposed on the wall (e.g., the ceiling of an operation room). The panel detector 730 may be disposed behind the support 710, and the panel detector 730 disposed on the column 720 may be capable of moving along the column 720. It may be understood that the manner of controlling the movement of the X-ray generation device 740 is not limited to using the mechanism arm 750 mounted on the ceiling. Other manners such as using the mechanism arm 750 attached to a supporting column that stands on the floor, or the like, may also be applicable.

When the scan is performed on the target region corresponding to the target portion of the subject, the subject may stand on the support 710 as shown in FIG. 7. The processing device 140 may determine the target region to be scanned according to the height data obtained from the historical medical record or a measurement of the height of the subject before the scan. The processing device 140 may determine the position of the X-ray generation device 740, for example, by aligning the X-ray generation device 740 with a center of the target region. The processing device 140 may further determine the movement of the X-ray generation device 740, for example, by determining an extent of stretching out or drawing back the mechanical arm 750 and an angle of the angular rotation of the X-ray generation device 740. The processing device 140 may further determine a distance by which the panel detector 730 (e.g., a flat panel detector) is moved along the column 720 to align with the target region. After the X-ray generation device 740 aligns with the target region, the doctor or the operator may send an instruction to the X-ray machine to start the scan. The X-rays may be emitted from a bulb in the X-ray generation device 740, and the panel detector 730 may receive at least a portion of the emitted X-rays, including those passing through the subject. The received signal may be used to generate an X-ray image of the target region.

It should be noted that the above description regarding the FIG. 7 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, instead of the X-ray machine shown in FIG. 7, the imaging device may be a CT scanner, an MR scanner, a PET scanner, etc. As another example, the subject may lie on a couch of the imaging device.

Figure 8:
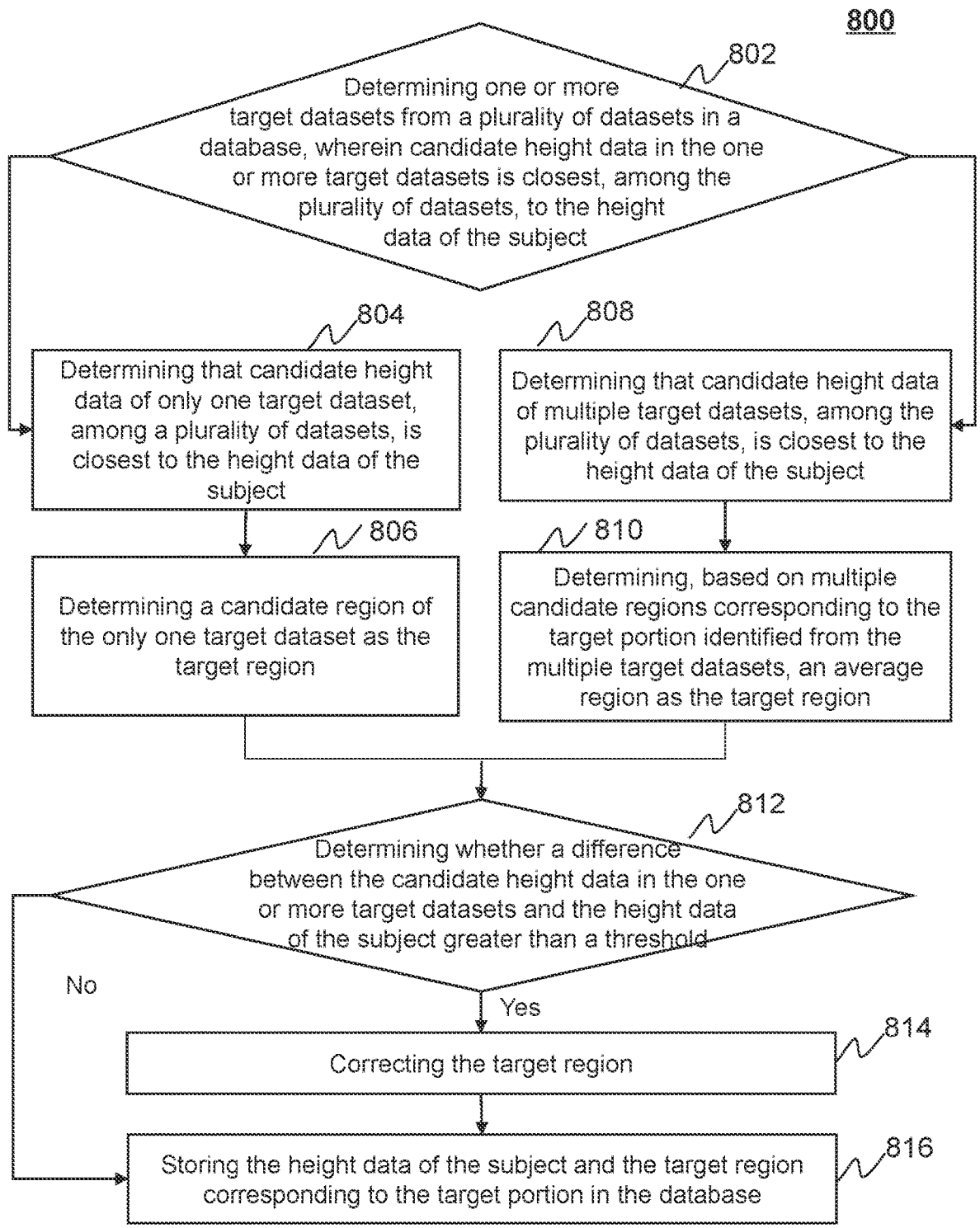
FIG. 8 is a flowchart illustrating an exemplary process for determining the target region associated with an imaging device according to some embodiments of the present disclosure.

FIG. 8 is a flowchart illustrating an exemplary process for determining the target region associated with an imaging device according to some embodiments of the present disclosure. In some embodiments, operation 604 may be performed according to operations 802-814 in the process 800 shown in FIG. 8. At least a portion of the process 800 may be implemented on the computing device 200 as illustrated in FIG. 2. In some embodiments, one or more operations of the process 800 may be implemented in the system 100 as illustrated in FIG. 1. In some embodiments, one or more operations in the process 800 may be stored in the storage device 150 (e.g., the non-volatile storage medium 230, the memory 260, etc.) as a form of instructions, and invoked and/or executed by the processing device 140, the processor 210 of the computing device 200, and/or one or more modules in FIG. 4. In some embodiments, the instructions may be transmitted in the form of electronic current or electrical signals.

In 802, the processing device 140 (e.g., the determination module 420) may determine one or more target datasets from a plurality of datasets in a database. Candidate height data in the one or more target datasets may be closest, among the plurality of datasets, to the height data of the subject. In some embodiments, the database may be stored in a local storage medium, such as a hard disk, or may be stored in a remote onlinestorage medium. The database may include a plurality of datasets. Each of the plurality of datasets may include candidate height data and a plurality of candidate regions corresponding to a plurality of candidate portions associated with the candidate height data. In some embodiments, to ensure a certain accuracy of the determination of the target region, the database may include a sufficient number (or count) of datasets. These datasets may be determined based on a plurality of historical medical records or scientific research. In some embodiments, each of the plurality of candidate regions corresponding to the height data and one of the plurality of candidate portions may be an average candidate region determined based on the plurality of historical medical records.

The processing device 140 may determine one or more target datasets from the plurality of datasets. The candidate height data in the one or more target datasets may be closest, among the plurality of datasets, to the height data of the subject. The precision level of the height data may be a centimeter level or a millimeter level. To determine the one or more target datasets, the processing device 140 may determine, for each of the plurality of datasets, an absolute value of a difference between the height data of the dataset and the height data of the subject. One or more datasets corresponding to the minimum absolute value of the difference may be determined as the one or more target dataset. For example, if the absolute value of the difference corresponding to a dataset is zero, that is, the height data of a dataset is the same as the height data of the subject, the dataset may be determined as one of the one or more target datasets. The processing engine may proceed to operation 804 or operation 808 based on a number count of the target datasets.

In 804, the processing device 140 (e.g., the determination module 420) may determine that candidate height data of only one target dataset, among a plurality of datasets, is closest to the height data of the subject. Then the processing device 140 may proceed to operation 806.

In 806, the processing device 140 (e.g., the determination module 420) may determine a candidate region of the only one target dataset as the target region. Then the processing device 140 may proceed to operation 812.

In 808, the processing device 140 (e.g., the determination module 420) may determine that candidate height data of multiple target datasets, among the plurality of datasets, is closest to the height data of the subject. Then the processing device 140 may proceed to operation 810.

In 810, the processing device 140 (e.g., the determination module 420) may determine, based on multiple candidate regions corresponding to the target portion identified from the multiple target datasets, an average region as the target region. Then the processing device 140 may proceed to operation 812.

The target region may be a region that includes the target portion on the body of the subject. For instance, the target region may be a rectangle. To determine the target region, the processing device 140 may determine a set of coordinates of a center of the target region, a first boundary of the target region that is relatively close to the head of the subject, and a second boundary of the target region that is relatively close to the feet of the subject. The processing device 140 may determine a first distance between the first boundary of the target region and the feet of the subject, and determine a second distance between the second boundary of the target region and the feet of the subject.

To determine an average region based on the multiple candidate regions, the processing device 140 may determine a set of coordinates of an average center based on multiple sets of coordinates of centers of the multiple candidate regions. The processing device 140 may determine a first average boundary based on the first boundaries of the multiple candidate regions and determine a second average boundary based on the second boundaries of the multiple candidate regions. The target region may be defined by the set of coordinates of the average center, the first average boundary, and the second average boundary.

In 812, the processing device 140 (e.g., the determination module 420) may determine whether a difference between the candidate height data in the one or more target datasets and the height data of the subject is greater than a threshold.

In some embodiments, the height data of the subject may be significantly different from the height data in the target dataset. For instance, when the subject is a dwarf or suffers from gigantism, the target region determined based on the one or more target datasets may be inaccurate. Therefore, the processing device 140 may compare the difference with a threshold. In response to a determination that the difference (i.e., an absolute value of the difference) is greater than the threshold, the processing device 140 may determine that the target region needs to be corrected. In response to a determination that the difference is less than or equal to the threshold, the processing device 140 may determine that the target region does not need to be corrected. The value of the threshold be a default value set in the system 100. For example, the value of the threshold may be set as 3 centimeters (cm), 2 cm, 1 cm, or the like.

In 814, the processing device 140 (e.g., the determination module 420) may correct the target region.

In some embodiments, the processing device 140 may automatically correct the target region. The target region may be enlarged or reduced according to a predetermined rule. The position of the center, the first boundary, or the second boundary of the target region to be scanned may be adjusted, thereby compensating for the difference between the height data of the target dataset and the height data of the subject. In some embodiments, a user (e.g., an operator or a doctor) may manually correct the target region.

In 816, the storage device 150 may store the height data of the subject and the target region corresponding to the target portion in the database.

In some embodiments, the height data of the subject and the target region corresponding to the target portion of the subject may be stored in the dataset to update the database for future use. Thus, an accuracy of determining the target region corresponding to the target portion of the same subject or another subject with the same height or a similar height may be improved.

Figure 9:
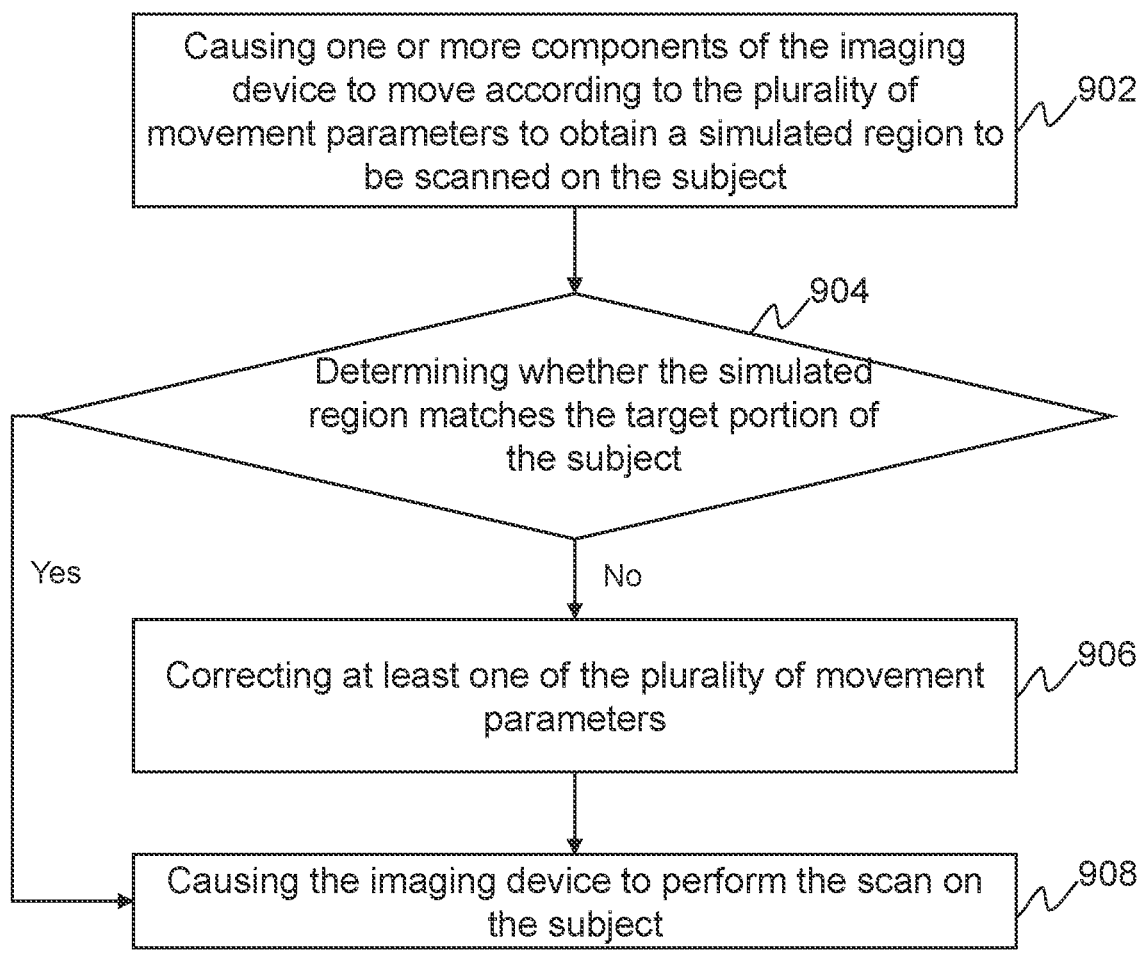
FIG. 9 is a flowchart illustrating an exemplary process for performing a scan on the subject based on the plurality of movement parameters associated with the imaging device according to some embodiments of the present disclosure.

FIG. 9 is a flowchart illustrating an exemplary process for performing a scan on the subject based on the plurality of movement parameters associated with the imaging device according to some embodiments of the present disclosure. At least a portion of process 900 may be implemented on the computing device 200 as illustrated in FIG. 2. In some embodiments, one or more operations of the process 900 may be implemented in the system 100 as illustrated in FIG. 1. In some embodiments, one or more operations in the process 900 may be stored in the storage device 150 (e.g., the non-volatile storage medium 230, the memory 260, etc.) as a form of instructions, and invoked and/or executed by the processing device 140, the processor 210 of the computing device 200, and/or one or more modules in FIG. 4. In some embodiments, the instructions may be transmitted in the form of electronic current or electrical signals.

In 902, the processing device 140 (e.g., the scanning module 430) may cause one or more components of the imaging device to move according to the plurality of movement parameters to obtain a simulated region to be scanned on the subject. The simulated region may be an actual region that the imaging device may scan. In some embodiments, the plurality of movement parameters determined based on the target region may not be suitable for the scan due to, for example, a significant difference between the target region determined by the processing device 140 and an actual region that covers the target portion of the subject. In order to ensure that the scan is performed on the target portion of the subject, the processing device 140 may perform a simulation process (e.g., the process 900). The processing device 140 may cause the one or more components of the imaging device (e.g., the mechanical arm of the X-ray machine, the couch of a CT scanner) to move according to the plurality of movement parameters to obtain a simulated region to be scanned on the subject. In some embodiments, during the simulation process, the panel detector (e.g., a flat panel detector) or the chest cassette of the X-ray machine does not need to be moved.

In some embodiments, in order to make it convenient for the operator to give an instruction to start the process 900, a simulation button may be set on the control interface of the terminal 130 or the imaging device. The operator may press the simulation button to cause the processing device 140 to perform the process 900. Then one or more components of the imaging device may be controlled to move based on the plurality of movement parameters.

In 904, the processing device 140 (e.g., the scanning module 430) may determine whether the simulated region matches the target portion of the subject. The simulated region may be identified by the processing device 140 and/or an operator. For example, the simulated region may be identified using a laser indicator. As another example, the simulation region may be identified using a beam limiter. The processing device 140 and/or the operator may determine whether the simulated region matches the target portion of the subject. In response to a determination that the simulated region matches the target portion of the subject, the processing device 140 may proceed to operation 908.

In 906, the processing device 140 (e.g., the scanning module 430) may correct at least one of the plurality of movement parameters. In some embodiments, the processing device 140 and/or the operator may correct a start position and/or an end position associated with the imaging device for the scan. For example, if the simulated region does not cover a part of the target portion of the subject, the processing device 140 may correct the start position and/or the end position so that the simulated region can be enlarged to cover all of the target portion of the subject. In some embodiments, if a plurality of sub-scans are needed to complete the scan on the target region (as described, for example, in operation 606), the processing device 140 may correct a plurality of start positions and a plurality of end positions corresponding to the plurality of sub-scans.

In 908, the processing device 140 (e.g., the scanning module 430) may cause the imaging device to perform the scan on the subject. In some embodiments, one or more components of the imaging device (e.g., an X-ray machine) may remain still during the scan. In some embodiments, one or more components of the imaging device (e.g., a cone beam CT scanner) may be controlled to move according to the plurality of movement parameters during the scan. An image reconstruction algorithm may be used to reconstruct an image of the target portion of the subject based on scan data obtained from the scan.

It should be noted that the above description regarding the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 10:
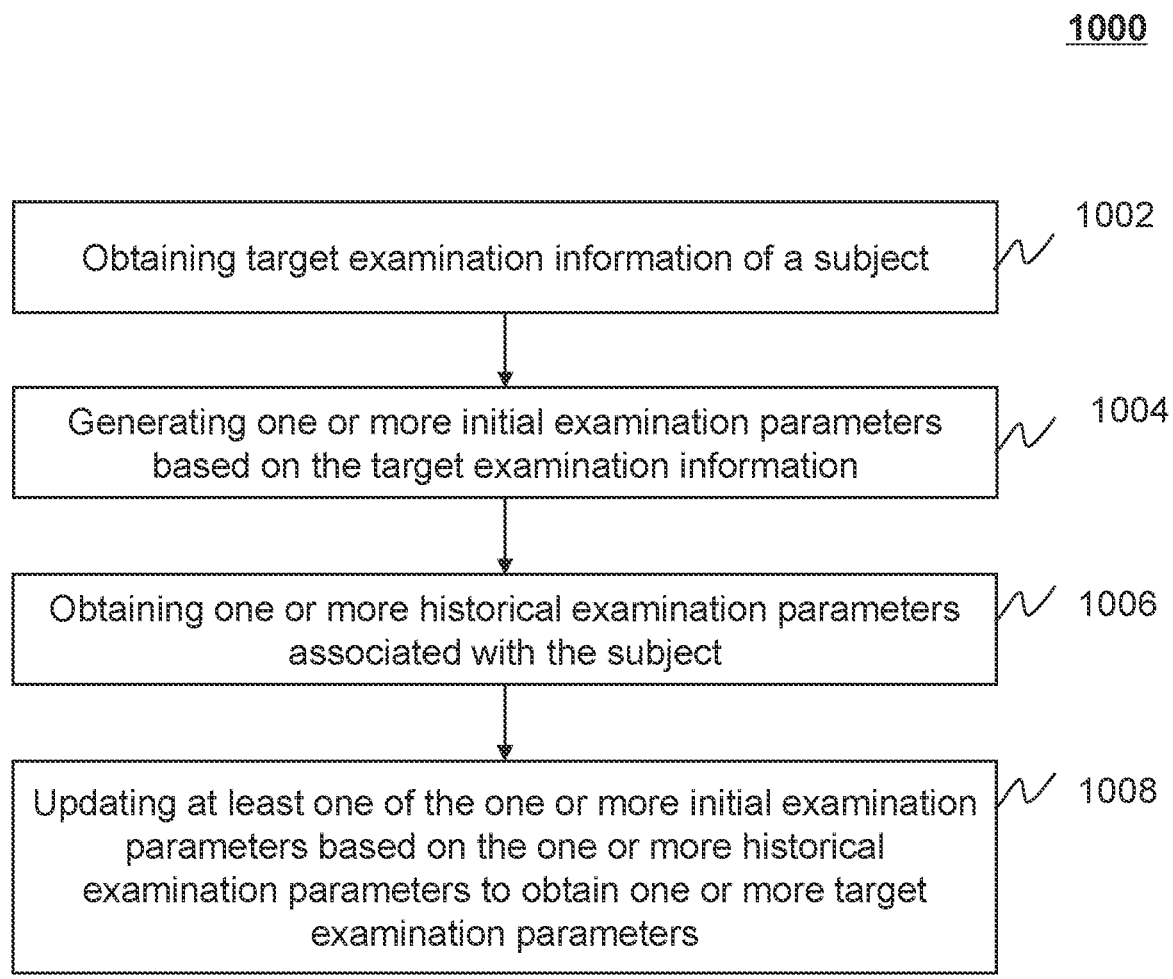
FIG. 10 is a flowchart illustrating an exemplary process for determining one or more target examinations for a target examination on a subject according to some embodiments of the present disclosure.

FIG. 10 is a flowchart illustrating an exemplary process for determining one or more target examinations for a target examination on a subject according to some embodiments of the present disclosure. At least a portion of process 1000 may be implemented on the computing device 200 as illustrated in FIG. 2. In some embodiments, one or more operations of the process 1000 may be implemented in the system 100 as illustrated in FIG. 1. In some embodiments, one or more operations in the process 1000 may be stored in the storage device 150 (e.g., the non-volatile storage medium 230, the memory 260, etc.) as a form of instructions, and invoked and/or executed by the processing device 140, the processor 210 of the computing device 200, or one or more modules in FIG. 5. In some embodiments, the instructions may be transmitted in the form of electronic current or electrical signals.

In 1002, the processing device 140 (e.g., the acquisition module 510) may obtain target examination information of a subject. In some embodiments, the target examination information of the subject may include personal information of the subject, for example, the identification number, the name, the age, the gender, the height, the weight, or the like. Additionally or alternatively, the target examination information of the subject may further include a type of a target examination to be performed on the subject and/or a target portion of the subject to be examined such as a lung, a leg, the stomach, etc. In some embodiments, the target examination information of the subject may be obtained before the target examination is performed on the subject. For instance, the subject may fill out an examination form to provide the target examination information to the system 100. As another example, an operator may input the target examination information via the terminal 130 for the subject. As yet another example, at least a portion of the target examination information may be obtained from a historical examination record of the subject, such as the gender, the age. In some embodiments, the target examination may be a medical examination intended to obtain health information of the subject. Merely by way of example, the target examination may be a scan on the subject using a medical imaging device.

In 1004, the processing device 140 (e.g., the parameter generation module 520) may generate one or more initial examination parameters based on the target examination information. As used herein, the term "examination parameter" refers to a technical parameter related to an examination protocol for the target examination. For instance, one or more examination parameters for a CT scan may include a tube voltage of a radiation source, a tube current of the radiation source, an irradiation field of a beam limiter, one or more position parameters related to the subject in the imaging device, a scanning mode (e.g., a helical scan, a non-helical scan), or the like, or any combination thereof. In some embodiments, there may be a plurality of sets of examination parameters corresponding to different target portions of the subject (e.g., a patient, an animal). The processing device 140 and/or a user (e.g., an operator) may select a set of examination parameters from the plurality of sets of examination parameters according to a part of the subject's need to check. The selected set of examination parameters may be designated as the one or more initial examination parameters. In some embodiments, the initial examination parameter may be unsuitable for the subject. For example, when a scan is performed on the subject, if the subject is relatively fat, a dose (i.e., an initial examination parameter) may be insufficient due to the thickness of the target portion of the subject. The operator may need to manually adjust a portion of the initial parameters and determine whether the adjusted examination parameters can be used in the target examination on the subject, which may complicate the work associated with the target examination. In order to simplify the work of the operator and improve an accuracy of target examination parameters used in the target examination, the processing device 140 may proceed to operation 1006.

In 1006, the processing device 140 (e.g., the acquisition module 510) may obtain one or more historical examination parameters associated with the subject. In some embodiments, the one or more historical examination parameters may correspond to the target examination information of the subject. The processing device 140 may obtain one or more first historical examination records associated with the subject. The one or more first historical examination records may correspond to different examination information of the subject. A doctor or an operator may have confirmed that the plurality of historical examination records of the subject can be used as a reference for the target examination. The processing device 140 may further determine whether the one or more first historical examination records include one or more second historical examination records matching the target examination information. In some embodiments, the processing device 140 may determine a matching degree between the target examination and historical examination information in the one or more first historical examination records. The processing device 140 may further compare the one or more matching degrees corresponding to the one or more first historical examination records with a matching degree threshold. The processing device 140 may designate the one or more first historical examination records of which the one or more matching degrees are greater than the matching degree threshold as the one or more second historical examination records.

In response to a determination that none of the one or more first historical examination records match the target examination information, the processing device 140 may designate the one or more initial examination parameters as the one or more target examination parameters. Alternatively, the operator may manually correct the one or more initial examination parameters to obtain the one or more target examination parameters. In response to a determination that only one second historical examination record matches the target examination information, the processing device 140 may obtain the one or more historical examination parameters from the only one second historical examination record. In response to a determination that multiple second historical examination records match the target examination information, the processing device 140 may assess, for each of the multiple second historical examination records, a degree of similarity between examination information of an examination corresponding to the second historical examination record and the target examination information. The processing device 140 may identify, from the multiple second historical examination records, a third historical examination record of an examination that has, among the one or more second historical examination records, a highest degree of similarity with the target examination information. The processing device 140 may obtain the one or more historical examination parameters from the third historical examination record. More details regarding obtaining the one or more historical examination parameters from the third historical examination record may be found elsewhere in the present disclosure, for example, in FIG. 11 and the description thereof.

In 1008, the processing device 140 (e.g., the parameter updating module 530) may update at least one of the one or more initial examination parameters based on the one or more historical examination parameters to obtain one or more target examination parameters. In some embodiments, the one or more historical examination parameters may be used as a reference for correcting at least one of the one or more initial examination parameters. In some embodiments, the one or more historical examination parameters may be used to replace at least one of the one or more initial examination parameters. In some embodiments, the processing device 140 may automatically correct or replace the at least one of the one or more initial examination parameters based on the one or more historical examination parameters. In some embodiments, the operator may manually correct or replace the at least one of the one or more initial examination parameters based on the one or more historical examination parameters. In some embodiments, the storage device 150 may store the one or more target examination parameters and the target examination information of the subject for future use.

A device (e.g., the device 110) may be used to perform the target examination on the subject. In some embodiments, the target examination may be a scan on the subject and the device 110 may be an imaging device. The target examination information of the subject may include height data and a target portion of the subject to be scanned by the imaging device. The one or more target examination parameters may include a target region corresponding to the target portion of the subject. The target portion of the subject may be within the target region. The processing device 140 may further determine, based on the target region, a plurality of movement parameters associated with the imaging device. The plurality of movement parameters may include at least one start position and at least one end position for the scan. In some embodiments, the processing device 140 may determine the plurality of movement parameters based on the target region of the subject and a position of the subject in the imaging device. More details regarding the determination of the plurality of movement parameters may be found elsewhere in the present disclosure, for example, in operation 606 of the process 600.

It should be noted that the above description regarding the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 11:
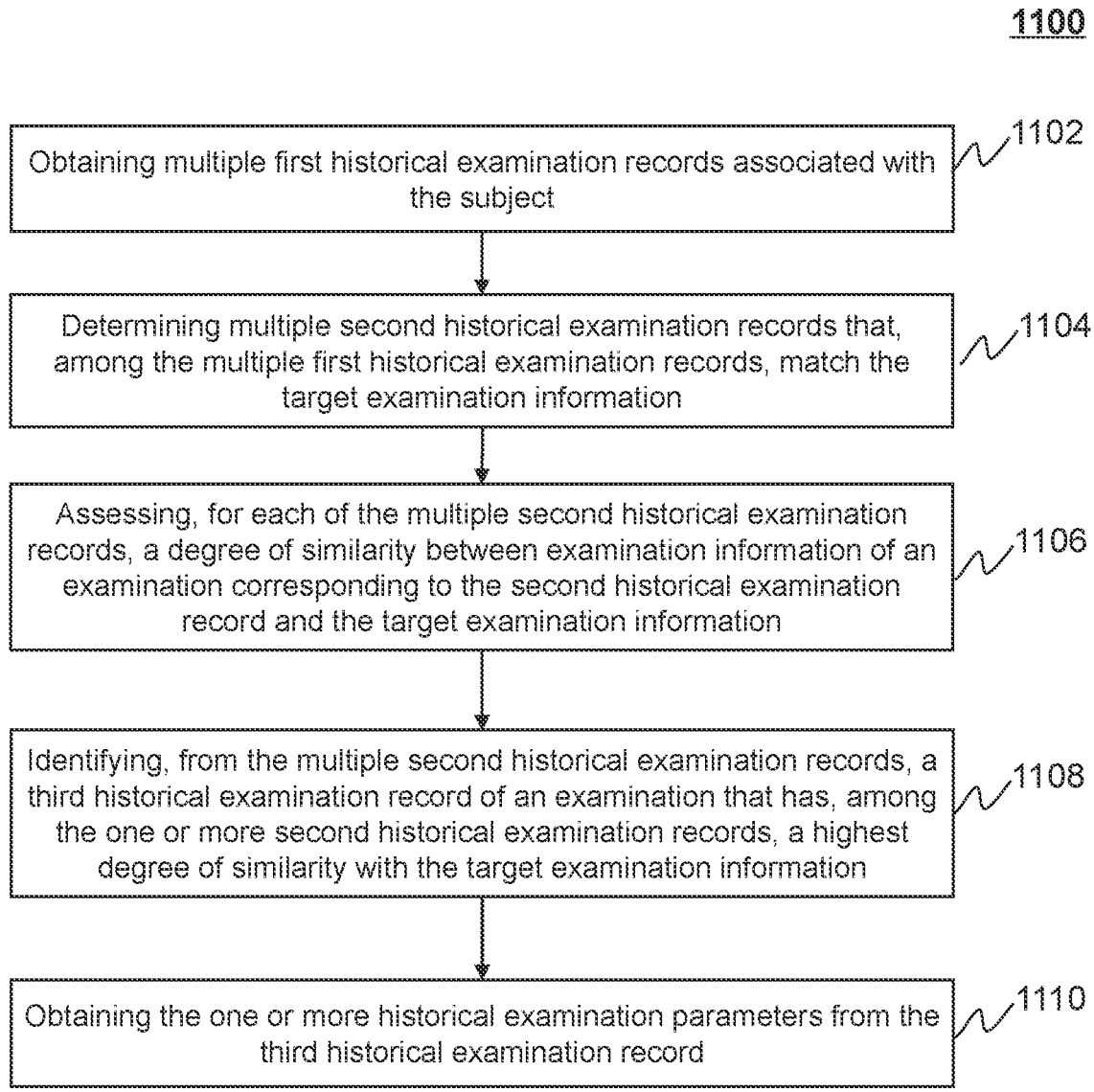
FIG. 11 is a flowchart illustrating an exemplary process for determining the one or more target examination parameters for the target examination on the subject based on multiple second historical examination records that match target examination of the subject according to some embodiments of the present disclosure.

FIG. 11 is a flowchart illustrating an exemplary process for determining the one or more target examination parameters for the target examination on the subject based on multiple second historical examination records that match target examination of the subject according to some embodiments of the present disclosure. At least a portion of process 1100 may be implemented on the computing device 200 as illustrated in FIG. 2. In some embodiments, one or more operations of the process 1100 may be implemented in the system 100 as illustrated in FIG. 1. In some embodiments, one or more operations in the process 1100 may be stored in the storage device 150 (e.g., the non-volatile storage medium 230, the memory 260, etc.) as a form of instructions, and invoked and/or executed by the processing device 140, the processor 210 of the computing device 200, or one or more modules in FIG. 5. In some embodiments, the instructions may be transmitted in the form of electronic current or electrical signals.

In 1102, the processing device 140 (e.g., the acquisition module 510) may obtain multiple first historical examination records associated with the subject. The one or more first historical examination records may match with the target examination information of the subject. The multiple first historical examination records may be stored in the storage device 150 in any form, such as a text description, a table, a graph, or the like, or any combination thereof. The processing device 140 may obtain the multiple first historical examination records from the storage device 150.

In 1104, the processing device 140 (e.g., the parameter updating module 530) may determine multiple second historical examination records that, among the one or more first historical examination records, match the target examination information. The target examination information may include one or more features, such as the age, the gender, the height of the subject, the target portion to be examined, or the like, or any combination thereof.

In 1106, the processing device 140 (e.g., the parameter updating module 530) may assess, for each of the multiple second historical examination records, a degree of similarity between examination information of an examination corresponding to the second historical examination record and the target examination information.

In 1108, the processing device 140 (e.g., the parameter updating module 530) may identify, from the multiple second historical examination records, a third historical examination record of an examination that has, among the multiple second historical examination records, a highest degree of similarity with the target examination information.

In some embodiments, in operation 1106, the processing device 140 may assess the degree of the similarity by comparing, for each of the multiple second historical examination records, a time when an examination corresponding to the second historical examination occurred and a time of the target examination. The time of the target examination may be a time when the target examination is to be performed. In some embodiments, a current time for performing the operation 1106 may be used to represent the time of the target examination. It may be understood that a status (e.g., physical conditions) of the subject in an examination that occurred at the time closest to the time of the target examination may be close to a status of the subject in the target examination. In operation 1108, the processing device 140 may identify a second historical examination record of an examination that, among the multiple second historical examination records, occurred at a time closest to the time of the target examination as the third historical examination record.

In some embodiments, in operation 1106, the processing device 140 may access the similarity by comparing, for each of the multiple second historical examination records, a parameter of interest of a device (e.g., a device model) used in an examination corresponding to the second historical examination record and a corresponding parameter of a device to be used in the target examination. The processing device 140 may determine the third historical examination record based on a result of the comparison. In some embodiments, the processing device 140 may determine a result that for each examination corresponding to one of the multiple second historical examination records, the parameter of interest of a device used therein is different from the corresponding parameter of the device to be used in the target examination. In response to such a result, the processing device 140 may compare a time when each of multiple examinations corresponding to the multiple second historical examination records occurred and a time of the target examination. In operation 1108, the processing device 140 may designate a second historical examination record of an examination that, among the multiple second historical examination records, occurred at a time closest to the time of the target examination as the third historical examination record.

In some embodiments, in operation 1106, the processing device 140 may determine a result that the parameter of interest of the device used in only one examination corresponding to one of the multiple second historical examination records is the same as the corresponding parameter of the device to be used in the target examination. In response to such a result, in operation 1108, the processing device 140 may designate a second historical examination record corresponding to the only one examination using the device whose parameter of interest is the same as the corresponding parameter of the device to be used in the target examination as the third historical examination record.

In some embodiments, in operation 1106, the processing device 140 may determine a result that for each of more than one examination that corresponds to more than one second historical examination record of the multiple second historical examination records, the parameter of interest of a device used therein is the same as the corresponding parameter of the device to be used in the target examination. As used herein, an examination that, among one or more examinations corresponding to the multiple second historical examination records that match the target examination, uses a device having a same parameter of interest as the target examination may be referred to as a "first examination." In response to such a result, the processing device 140 may compare a time when each of the more than one first examination occurred and a time of the target examination. In 1108, the processing device 140 may designate a second historical examination record of an examination that, among the more than one second historical examination record corresponding to the more than one first examination, occurred at a time closest to the time of the target examination as the third historical examination record.

In some embodiments, in operation 1106, in response to the result that for each of the more than one first examination, the parameter of interest of the device used therein is the same as the corresponding parameter of the device to be used in the target examination, the processing device 140 may compare, in operation 1108, for each of the more than one first examination, at least one position parameter associated with the subject used in the first examination and at least one position parameter associated with the subject to be used in the target examination. The processing device 140 may further determine whether for only one first examination among the more than one first examination, the at least one position parameter associated with the subject used therein is the same as the at least one position parameter associated with the subject to be used in the target examination. In response to a determination that for only one first examination among the more than one first examination, at least one position parameter associated with the subject used therein is the same as the at least one position parameter associated with the subject to be used in the target examination, the processing device 140 may designate a second historical examination record corresponding to the only one first examination as the third historical examination record.

In some embodiments, in operation 1108, the processing device 140 may determine whether for each of multiple first examinations among the more than one first examination, at least one position parameter associated with the subject used therein is the same as the at least one position parameter associated with the subject to be used in the target examination. In response to a result that for each of multiple first examinations among the more than one first examination, at least one position parameter associated with the subject used therein is the same as the at least one position parameter associated with the subject to be used in the target examination, the processing device 140 may further compare a time when each of the multiple first examinations occurred and a time of the target examination. The processing device 140 may designate a second historical examination record of an examination that, among the more than one second historical examination record corresponding to the more than one examination each using a device whose parameter of interest is the same as the corresponding parameter of the device to be used in the target examination, occurred at a time closest to the time of the target examination as the third historical examination record.

In some embodiments, in operation 1108, the processing device 140 may determine whether for each of the more than one first examination, the at least one position parameter associated with the subject used therein is different from the at least one position parameter associated with the subject to be used in the target examination. In response to a determination that for each of the more than one first examination, the at least one position parameter associated with the subject used therein is different from the at least one position parameter associated with the subject to be used in the target examination, the processing device 140 may compare the time when each of the more than one first examinations occurred and a time of the target examination. The processing device 140 may designate a second historical examination record of an examination that, among the more than one first examination each using a device whose parameter of interest is the same as the corresponding parameter of the device to be used in the target examination, occurred at a time closest to the time of the target examination as the third historical examination record.

In 1110, the processing device 140 (e.g., the parameter updating module 530 or the acquisition module 510) may obtain the one or more historical examination parameters from the third historical examination record. The one or more historical examination parameters may be used as a reference for determining the one or more target historical parameters. The processing device 140 and/or the user may obtain the one or more target historical parameters by updating at least one of the one or more initial historical examination parameters based on the historical examination parameters.

It should be noted that the above description regarding the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for determining one or more target examination parameters, implemented on a computing device having at least one processor and at least one non-transitory storage medium, the method comprising:
   obtaining target examination information of a subject;
   generating one or more initial examination parameters based on the target examination information;
   obtaining one or more first historical examination records associated with the subject;
   determining whether the one or more first historical examination records include one or more second historical examination records matching the target examination information;
   in response to a determination that the one or more first historical examination records include one or more second historical examination records matching the target examination information, obtaining one or more historical examination parameters from the one or more second historical examination records; and
   updating at least one of the one or more initial examination parameters based on the one or more historical examination parameters to obtain one or more target examination parameters, wherein the one or more target examination parameters are used for performing a target examination on the subject.

2. A system for determining one or more target examination parameters, comprising:
   at least one non-transitory storage medium including a set of instructions; and
   at least one processor in communication with the at least one non-transitory storage medium, wherein when executing the set of instructions, the at least one processor is directed to cause the system to:
      obtain target examination information of a subject;
      generate one or more initial examination parameters based on the target examination information;
      obtain one or more first historical examination records associated with the subject;
      determine whether the one or more first historical examination records include one or more second historical examination records matching the target examination information;

in response to a determination that the one or more first historical examination records include one or more second historical examination records matching the target examination information, obtain one or more historical examination parameters from the one or more second historical examination records; and update at least one of the one or more initial examination parameters based on the one or more historical examination parameters to obtain one or more target examination parameters, wherein the one or more target examination parameters are used for performing a target examination on the subject.

3. The system of claim 2, wherein to obtain the one or more historical examination parameters from the one or more second historical examination records, the at least one processor is directed to cause the system to:

determine whether only one second historical examination record matches the target examination information; and in response to a determination that only one second historical examination record matches the target examination information, obtain the one or more historical examination parameters from the only one second historical examination record.

4. The system of claim 2, wherein to obtain the one or more historical examination parameters from the one or more second historical examination records, the at least one processor is directed to cause the system to:

assess, for each of the one or more second historical examination records, a degree of similarity between examination information of an examination corresponding to the second historical examination record and the target examination information;

identify, from the one or more second historical examination records, a third historical examination record of an examination that has, among the one or more second historical examination records, a highest degree of similarity with the target examination information; and obtain the one or more historical examination parameters from the third historical examination record.

5. The system of claim 4, wherein to assess, for each of the one or more second historical examination records, the degree of similarity between examination information of an examination corresponding to the second historical examination record and the target examination information, the at least one processor is directed to cause the system to compare, for each of the one or more second historical examination records, a time when an examination corresponding to the second historical examination record occurred and a time of the target examination; and to identify the third historical examination record of the examination that has, among the one or more second historical examination records, the highest degree of similarity with the target examination information, the at least one processor is directed to cause the system to designate a second historical examination record of an examination that, among the one or more second historical examination records, occurred at a time closest to the time of the target examination as the third historical examination record.

6. The system of claim 4, wherein to assess, for each of the one or more second historical examination records, the degree of similarity between examination information of an examination corresponding to the second historical examination record and the target examination information, the at least one processor is directed to cause the system to compare, for each of the one or more second historical examination records, a parameter of interest of a device used in an examination corresponding to the second historical examination record and a corresponding parameter of a device to be used in the target examination.

7. The system of claim 6, wherein to compare, for each of the one or more second historical examination records, a parameter of interest of a device used in an examination corresponding to the second historical examination record and a corresponding parameter of a device to be used in the target examination, the at least one processor is directed to cause the system to determine whether for each examination that corresponds to one of the one or more second historical examination records, the parameter of interest of a device used therein is different from the corresponding parameter of the device to be used in the target examination; and in response to a determination that for each examination that corresponds to one of the one or more second historical examination records, the parameter of interest of the device used therein is different from the corresponding parameter of the device to be used in the target examination, compare a time when each of one or more examinations corresponding to the one or more second historical examination records occurred and a time of the target examination; and to identify the third historical examination record of the examination that has, among the one or more second historical examination records, the highest degree of similarity with the target examination information, the at least one processor is directed to cause the system to designate a second historical examination record of an examination that, among the one or more second historical examination records, occurred at a time closest to the time of the target examination as the third historical examination record.

8. The system of claim 6, wherein to compare the parameter of interest of the device used in the examination corresponding to each of the one or more second historical examination records and the corresponding parameter of a device to be used in the target examination, the at least one processor is directed to cause the system to determine whether the parameter of interest of a device used in only one examination corresponding to one of the one or more second historical examination records is the same as the corresponding parameter of the device to be used in the target examination, and to identify the third historical examination record of the examination that has, among the one or more second historical examination records, the highest degree of similarity with the target examination information, the at least one processor is directed to cause the system to designate a second historical examination record corresponding to the only examination using the device whose parameter of interest is the same as the corresponding parameter of the device to be used in the target examination as the third historical examination record.

9. The system of claim 6, wherein to compare the parameter of interest of the device used in the examination corresponding to each of the one or more second historical examination records and the corresponding parameter of the device to be used in the target examination, the at least one processor is directed to cause the system to determine whether for each of more than one examination that corresponds to more than one second historical examination record of the one or more second historical examination records, the parameter of interest of a device used therein is the same as the corresponding parameter of the device to be used in the target examination, and in response to a determination that for each of more than one examination that corresponds to more than one second historical examination of the one or more second historical examination records, the parameter of interest of the device used therein is the same as the corresponding parameter of the device to be used in the target examination, compare a time when each of the more than one examination occurred and a time of the target examination; and to identify the third historical examination record of the examination that has, among the one or more second historical examination records, the highest degree of similarity with the target examination information, the at least one processor is directed to cause the system to:

designate a second historical examination record of an examination that, among the more than one second historical examination record corresponding to the more than one examination each using the device whose parameter of interest is the same as the corresponding parameter of the device to be used in the target examination, occurred at a time closest to the time of the target examination as the third historical examination record.

10. The system of claim 6, wherein to compare, for each of the one or more second historical examination records, the parameter of interest of a device used in an examination corresponding to the second historical examination record and the corresponding parameter of a device to be used in the target examination, the at least one processor is directed to cause the system to determine whether, for each of more than one examination that corresponds to more than one second historical examination record of the one or more second historical examination records, the parameter of interest of a device used therein is the same as the corresponding parameter of the device to be used in the target examination, and in response to a determination that for each of more than one examination that corresponds to more than one second historical examination record of the one or more second historical examination records, the parameter of interest of the device used therein is the same as the corresponding parameter of the device to be used in the target examination, compare, for each of the more than one examination, at least one position parameter associated with the examination and at least one position parameter associated with the subject to be used in the target examination; and to identify the third historical examination record of an examination that has, among the one or more second historical examination records, the highest degree of similarity with the target examination information, the at least one processor is directed to cause the system to determine whether for only one examination among the more than one examination each using the device whose parameter of interest is the same as the corresponding parameter of the device to be used in the target examination, at least one position parameter associated with the subject used therein is the same as the at least one position parameter associated with the subject to be used in the target examination, and in response to a determination that for only one examination among the more than one examination each using the device whose parameter of interest is the same as the corresponding parameter of the device to be used in the target examination, at least one position parameter associated with the subject used therein is the same as the at least one position parameter associated with the subject to be used in the target examination, designate a second historical examination record corresponding to the only one examination as the third historical examination record.

11. The system of claim 6, wherein:

to compare, for each of the one or more second historical examination records, the parameter of interest of a device used in an examination corresponding to the second historical examination record and the corresponding parameter of a device to be used in the target examination, the at least one processor is directed to cause the system to determine whether for each of more than one examination that corresponds to more than one second historical examination of the one or more second historical examination records, the parameter of interest of a device used therein is the same as the corresponding parameter of the device to be used in the target examination, and in response to a determination that for each of more than one examination that corresponds to more than one second historical examination of the one or more second historical examination records, the parameter of interest of the device used therein is the same as the corresponding parameter of the device to be used in the target examination, compare at least one position parameter associated with the subject in the more than one examination and at least one position parameter associated with the subject in the target examination; and to identify the third historical examination record of an examination that has, among the one or more second historical examination records, the highest degree of similarity with the target examination information, the at least one processor is directed to cause the system to determine whether for each of multiple examinations among the more than one examination each using a device whose parameter of interest is the same as the corresponding parameter of the device to be used in the target examination, at least one position parameter associated with the subject used therein is the same as the at least one position parameter associated with the subject to be used in the target examination, and in response to a determination that for each of multiple examinations among the more than one examination each using the device whose parameter of interest is the same as the corresponding parameter of the device to be used in the target examination, at least one position parameter associated with the subject used therein is the same as the at least one position parameter associated with the subject to be used in the target examination, compare a time when each of the multiple examinations occurred and a time of the target examination, and designate a second historical examination record of an examination that, among the multiple examinations each using the device whose parameter of interest is the same as the corresponding parameter of the device to be used in the target examination and having at least one position parameter associated with the subject that is the same as the at least one position parameter associated with the subject to be used in the target examination, occurred at a time closest to the time of the target examination as the third historical examination record.

12. The system of claim 6, wherein:

to compare, for each of the one or more second historical examination records, the parameter of interest of a device used in an examination corresponding to the second historical examination record and a corresponding parameter of a device to be used in the target examination, the at least one processor is directed to cause the system to determine whether for each of more than one examination that corresponds to more than one of the one or more second historical examination records, the parameter of interest of a device used therein is the same as the corresponding parameter of the device to be used in the target examination, and in response to a determination that for each of more than one examination that corresponds to more than one of the one or more second historical examination records, the parameter of interest of the device used therein is the same as the corresponding parameter of the device to be used in the target examination, compare at least one position parameter associated with the subject in the more than one examination and at least one position parameter associated with the subject in the target examination; and to identify the third historical examination record of the examination that has, among the one or more second historical examination records, the highest degree of similarity with the target examination information, the at least one processor is directed to cause the system to determine whether for each examination of the more than one examination each using the device whose parameter of interest is the same as the corresponding parameter of the device to be used in the target examination, at least one position parameter associated with the subject used therein is different from the at least one position parameter associated with the subject to be used in the target examination, and in response to a determination that for each examination of the more than one examination each using the device whose parameter of interest is the same as the corresponding parameter of the device to be used in the target examination, at least one position parameter associated with the subject used therein is different from the at least one position parameter associated with the subject to be used in the target examination, compare a time when each of the multiple examinations occurred and a time of the target examination, and designate a second historical examination record of an examination that, among the more than one second historical examination record corresponding to the more than one examination each using a device whose parameter of interest is the same as the corresponding parameter of the device to be used in the target examination, occurred at a time closest to the time of the target examination as the third historical examination record.

13. The system of claim 6, wherein the parameter of interest of the device includes a device model.

14. The system of claim 2, wherein the at least one processor is further directed to cause the system to:

store the one or more examination parameters of the target examination of the subject.

15. The system of claim 2, wherein the target examination is a scan on the subject by an imaging device;

the target examination information of the subject includes height data and a target portion of the subject to be scanned by the imaging device; and the one or more target examination parameters include a target region corresponding to the target portion of the subject, wherein the target portion is within the target region.

16. The system of claim 15, wherein the at least one processor is further directed to cause the system to:

determine, based on the target region, a plurality of movement parameters associated with the imaging device, wherein the plurality of movement parameters include at least one start position and at least one end position associated with one or more components of the imaging device.

17. The system of claim 16, wherein to determine, based on the target region, the plurality of movement parameters associated with the imaging device, the at least one processor is directed to cause the system to:

determine a position of the subject in the imaging device; and determine the plurality of movement parameters based on the target region and the position of the subject in the imaging device.

18. The system of claim 16, wherein the at least one processor is further directed to cause the system to:

cause one or more components of the imaging device to move according to the plurality of movement parameters to obtain a simulated region to be scanned on the subject;

determine whether the simulated region matches the target portion of the subject; and in response to a determination that the simulated region does not match the target portion of the subject, correct at least one of the plurality of movement parameters.

19. A non-transitory computer readable medium, comprising at least one set of instructions for determining one or more target examination parameters, wherein when executed by at least one processor of a computing device, the at least one set of instructions direct the at least one processor to:

obtain target examination information of a subject;

generate one or more initial examination parameters based on the target examination information;

obtain one or more first historical examination records associated with the subject;

determine whether the one or more first historical examination records include one or more second historical examination records matching the target examination information;

in response to a determination that the one or more first historical examination records include one or more second historical examination records matching the target examination information, obtain one or more historical examination parameters from the one or more second historical examination records; and update at least one of the one or more initial examination parameters based on the one or more historical examination parameters to obtain one or more target examination parameters, wherein the one or more target examination parameters are used for performing a target examination on the subject.

* * * * *